US007300520B2

(12) United States Patent
Kwong et al.

(10) Patent No.: US 7,300,520 B2
(45) Date of Patent: Nov. 27, 2007

(54) CRYSTALLIZATION REAGENT MATRICES AND RELATED METHODS AND KITS

(75) Inventors: Peter D. Kwong, Washington, DC (US); Shahzad Majeed, Columbia, MD (US)

(73) Assignee: The Trustees of Columbia University in the City of New York, New York, NY (US)

( * ) Notice: Subject to any disclaimer, the term of this patent is extended or adjusted under 35 U.S.C. 154(b) by 248 days.

(21) Appl. No.: 10/887,663

(22) Filed: Jul. 9, 2004

(65) Prior Publication Data
US 2006/0099572 A1    May 11, 2006

Related U.S. Application Data

(60) Provisional application No. 60/485,798, filed on Jul. 9, 2003.

(51) Int. Cl.
*C30B 29/54* (2006.01)
(52) U.S. Cl. ............... 117/201; 117/68; 117/202; 422/245.1
(58) Field of Classification Search ............ 117/201, 117/202, 68; 422/245.1
See application file for complete search history.

(56) References Cited

U.S. PATENT DOCUMENTS

2005/0205006 A1* 9/2005 Segelke et al. ............ 117/206

2006/0111555 A1* 5/2006 Hoffmann ............... 530/350

FOREIGN PATENT DOCUMENTS

WO    WO 2005/005653 A2    1/2005

OTHER PUBLICATIONS

Audic, S. et al. (1997) "SAmBA: An Interactive Software of Optimizing the Design of Biological Macromolecules Crystallization Experiments" *Genetics* 29:252-257.
Askonas, B. (1950) "The Use of Organic Solvents at Low Temperature for the Separation of Enzymes. Applications to Aqueous Rabbit Muscle Extract" *Biochemical J.* 48:42-48.
Brünger, A.T. et al. (1998) "Crystallography & NMR System: A New Software Suite for Macromolecular Structure Determination" *Acta Cryst.* 905-921.
Carter, C.W. et al. (1979) "Protein Crystallization Using Incomplete Factorial Experiments" 254(23):12219-12223.
Collier, R.J. et al. (1981) "X-ray Grade Crystals of Diphtheria Toxin" *J. of Biol. Chemistry* 257(9):5283-5285.
Collier, R.J. (1982) "Crystalization of Exotoxin A From Pseudomas Aeruginosa" *J. Mol. Biol.* 157:413-415.
Crick, F.H.C. (1953) "The Unit Cells of Four Proteins" 6:221-222.
Forsythe, E.L. (1999) "Crystallization of Chicken Egg White Lysozyme from Assorted Sulfate Salts" 332-343.
Gilliland, G.L. (2002) "The Biological Macromolecule Crystallization Database: Crystalization Procedures and Strategies" *Acta Crystallogr.* D50, 916-920.

(Continued)

*Primary Examiner*—Robert Kunemund
(74) *Attorney, Agent, or Firm*—John P. White; Cooper & Dunham LLP

(57) ABSTRACT

This invention provides methods, kits and automated systems for identifying a reagent in which a compound crystallizes, and methods for crystallizing a compound.

59 Claims, 2 Drawing Sheets

OTHER PUBLICATIONS

Goodwill, K.E. et al. (2001) "High-throughtput X-ray Crystallography for Structure-based Drug Design" *Drug Discovery Today* 6, S113-S118.

Haas, D.J. (1967) "Preliminary X-ray Data for Two New Forms of Hen Egg-white Lysozyme" *Acta Crystl.* 23:666.

Hendrickson, W.A. (2000) "Synchrotron Crystallography" *TIBS* 637-643.

Jancarik, J. et al. (1991) "Sparse Matriz Sampling: A Screening Method for Crystallization of Proteins" *J. Appl. Cryst.* 24:409-411.

Kuciel, R. et al. (1992) "Crystallization of Human Prostactic Acid Phosphatase Using Biphasic Systems" *J. of Crystal Growth* 122:199-203.

Kwong, P.D. et al. (2000) "Structures of HIV-1 gp120 Envelope Glycoproteins from Laboratory-Adapted and Primary Isolates" *Structure* 8:1329-1339 Kwong, P.D. et al. (2000) "Structures of HIV-1 gp120 Envelope Glycoproteins from Laboratory-Adapted and Primary Isolates" *Structure* 8:1329-1339.

Kwong, P.D. et al. (1998) "Structure of an HIV gp120 Envelope Glycoprotein in complex with the CD4 Receptor and a Neutralizing Human Antibody" *Nature* 393:648-659.

Kwong, P.D. et al. (1990) "Molecular Characteristics of Recombinant Human CD4 as Deduced from Polymorphic Crystals" *Proc. Natl. Acad. Sci. USA* 87:6423-6427.

Kwong, P.D. et al. (1999) Probability Analysis of Variational Crystallization and Its Application to gp120, The Exterior Envelope Glycoprotein of Type 120, The Exterior Envelope Glycoprotein of Type 1 Human Immunodeficiency Virus (HIV-1).

Song, L. et al. (1997) "Membrane Protein Crystallization: Application of Sparse Matrices to the α-Hemolysin Heptamer" *Methods in Enzymology* 276:60-74.

Lim, K. et al. (1998) "Locations of Bromide Ions in Tetragonal Lysozyme Crystal" *Acta Cryst.* D54, 899-904.

Majeed, S. et al. (2003) "Enhancing Protein Crystallization Through Precipitant Synergy" *Structure* 11:1061-1070.

McPherson, A. (1976) "Crystallization of Proteins from Polyetheylene Glycol" *The J. of Biological Chemistry* 251(20):6300-6303.

McPherson, A. (2001) "A Comparison of Salts for the Crystallization of Macromolecules" *Protein Science* 10:418-422.

Navaza, J. (1994) "AMoRe: an Automated Package for Molecular Replacement" *Acta Cryst.* A50, 157-163.

Nicholls, A. et al. (1991) "Protein Folding and Association: Insights from the Interfacial and Thermodynamic Properties of Hydrocarbons" *Proteins: Structure, Functions, and Genetics* 11:281-296.

Otwinowski, Z. et al. (1997) "Processing of X-ray Diffraction Data Collected in Oscillation Mode" *Methods in Enzymology* 276:307-326.

Patel, S. et al. (1995) "Polymeric Precipitants for the Crystallization of Macromolecules" *Biochemical and Biophysical Research Communications* 207(2):819-828.

Polson, A. et al. (1964) "The Fractionation of Protein Mixtures by Linear Polymers of High Molecular Weights" *Biochim. Biophys. Acta* 82:463-475.

Qian et al. (2000) "A Rational Approach Towards Successful Crystallization and Crystal Treatment of Human Cytomegalovirus Protease and its Inhibitor Complex" *Acta Crystallographica* D56, 175-180.

Radaev, S. et al. (2002) "Crystalliztion of Protein-Protein Complexes" *J. Crystallogr.* 35:674-676.

Ray, W. et al. (1986) "The Effect of Polyethylene Glycol on the Growth and Dissolution Rates of a Crystalline Protein at High Salt Concentration" *J. of Biol. Chemistry* 261(25):11544-11549.

Sauter, C. et al. (2001) "Structure of Tetragonal Hen Egg-white Lysozyme at 0.94 Å from Crystals Grown by the Counter-Diffusion Method" *Acta Crystallographica* D57, 1119-1126.

Shapiro, L. et al. (1998) "The Argonne Structural Genomics Workshop: Lamaze Class for the Birth of a New Science" *Structure* 6;265-267.

Shapire, E.O. et al. (2001) "Crystal Structure of a Neutralizing Human IgG Aganinst HIV-1: A Template for Vaccine Design" *Science* 293:1155-1159.

Shieh, H. et al. (1995) "Using Sampling Techniques in Protein Crystallization" *Acta Crystallographica* D51, 305-310.

Segelke, B.W. (2001) "Efficiency Analysis of Sampling Protocols Used in Protein Crystallization Screening" *J. of Crystal Growth* 232:553-562.

Sousa, R. (1997) "Using Cosolvents to Stabilize Protein Conformation for Crystallization" *Methods in Enzymology* 276:131-143.

Stevens R. et al. (2001) "Industrializing Structural Biology" *Science* 293:519-520.

Steinrauf, L.K. et al. (1959) "Preliminary X-Ray Data for Some New Crystalline Forms of β-Lactoglobulin and Hen Egg-white Lysozyme" *Acta Crystallographica* 12:77-79.

Timasheff, S.N. et al. (1988) "Mechanism of Protein Precipitation and Stabilization by Co-Solvents" *J. of Crystal Growth* 90:39-46.

Vaney, M.C. et al. (2001) "Structural Effects of Monovalent Anions on Polymorphic Lysozyme Crystal" *Acta Crystallographica* D57, 929-940.

Wu, H. et al. (1997) "Dimeric Association and Segmental Variability in the Structure of Human CD4" *Nature* 387:527-530.

Wukovitz et al. (1995) "Why Protein Crystals Favour Some Space-Groups Over Others" *Nature* 2(12):1062-1067.

PCT International Search Report issued Feb. 16, 2007 in connection with PCT International Application No. PCT/US2004/021975, filed Jul. 9, 2004, International Publication No. WO 2005/005653 A2, published Jan. 20, 2005, on behalf of The Trustees of Columbia University in the City of New York.

Written Opinion issued Feb. 16, 2007 in connection with PCT International Application No. PCT/US2004/021975, filed Jul. 9, 2004, International Publication No. WO 2005/005653 A2, published Jan. 20, 2005, on behalf of The Trustees of Columbia University in the City of New York.

International Preliminary Report On Patentability issued Mar. 22, 2007 in connection with PCT International Application No. PCT/US2004/021975, filed Jul. 9, 2004, International Publication No. WO 2005/005653 A2, published Jan. 20, 2005, on behalf of The Trustees of Columbia University in the City of New York.

* cited by examiner

CRYSTALLIZATION REAGENT MATRICES AND RELATED METHODS AND KITS

This application claims priority of U.S. provisional application No. 60/485,798, filed Jul. 9, 2003, the contents of which are hereby incorporated by reference.

Throughout this application, various publications are referenced by Arabic numerals. Full citations for these publications may be found listed at the end of the specification immediately preceding the claims. The disclosures of these publications in their entireties are hereby incorporated by reference into this application in order to more fully describe the state of the art as of the date of the invention described and claimed herein.

BACKGROUND OF THE INVENTION

Over the last decade, the number of macromolecular structures determined by X-ray diffraction has increased dramatically, driven by revolutions in a number of supporting technologies [1-3]. An absolutely essential part of the process, crystallization, is still not fully understood (reviewed in [4, 5]).

Two theoretical innovations, incomplete factorial analysis [6] and sparse matrix screening [7], introduced the idea of analyzing combinations of independent factors that affect crystallization. Widespread success with the latter suggested that, once at the precipitation point, having the proper combination of factors is more important than subtle variation in the concentration of any single factor. Still, success with sparse matrix screening is intimately tied to the choice of independent factors upon which the matrix is based. In both the original incomplete factorial and sparse matrix analyses [6, 7], the precipitating agent was treated as a single independent variable. But precipitating agents can function by altering the activity coefficient of water (salts) [8], by altering the dielectric constant of the solvating medium (organic solvents) [9] or by increasing molecular crowding (high molecular weight polymers like polyethylene glycol [PEG]) [10, 11]. The notion of precipitant combinations has been speculated upon (for example by Carter in [12]), but never experimentally developed or tested.

SUMMARY OF THE INVENTION

This invention provides a method for identifying a reagent in which a compound crystallizes, comprising the steps of:
  (a) contacting the compound with a matrix of reagents, wherein
     (i) the reagents collectively comprise a first type of precipitating agent which alters the activity coefficient of water, a second type of precipitating agent which increases the molecular crowding of a compound in solution, and a third type of precipitating agent which reduces the dielectric of a solution solvating the compound;
     (ii) each reagent comprises two precipitating agents selected from the first, second and third type of precipitating agents, wherein the two precipitating agents are of a different type; and
     (iii) for each of the first, second and third types of precipitating agent, the matrix comprises at least two reagents differing from one another in that they comprise different species of, or different concentrations of, the type of precipitating agent; and
  (b) after a suitable period of time, identifying one of the reagents, if any, in which the compound has crystallized, thereby identifying a reagent in which the compound crystallizes.

This invention further provides a method for crystallizing a compound comprising the steps of contacting the compound with a reagent for a suitable period of time, wherein the reagent has been identified, according to the instant method, as a reagent in which the compound crystallizes.

This invention further provides a first kit for use in identifying a reagent in which a compound crystallizes, comprising a matrix of reagents wherein
  (i) the reagents collectively comprise a first type of precipitating agent which alters the activity coefficient of water, a second type of precipitating agent which increases the molecular crowding of a compound in solution, and a third type of precipitating agent which reduces the solvent dielectric of a solution solvating the compound;
  (ii) each reagent comprises two precipitating agents selected from the first, second and third type or precipitating agents, wherein the two precipitating agents are of a different type; and
  (iii) for each of the first, second and third types of precipitating agent, the matrix comprises at least two reagents differing from one another in that they comprise different species of, or different concentrations of, the type of precipitating agent.

This invention further provides a second kit for use in identifying a reagent in which a compound crystallizes, which kit comprises a matrix of discrete combinations of agents, wherein
  (i) each discrete combination of agents, when combined with a predetermined amount of water, forms a reagent in which the agents are in solution at a predetermined concentration;
  (ii) the reagents, once formed, collectively comprise a first type of precipitating agent which alters the activity coefficient of water, a second type of precipitating agent which increases the molecular is crowding of a compound in solution, and a third type of precipitating agent which reduces the solvent dielectric of a solution solvating the compound;
  (iii) each reagent, once formed, comprises two precipitating agents selected from the first, second and third type of precipitating agents, wherein the two precipitating agents are of a different type; and
  (iv) once reagents are formed, for each of the first, second and third types of precipitating agent, the matrix comprises at least two reagents differing from one another in that they comprise different species of, or different concentrations of, the type of precipitating agent.

Finally, this invention provides an automated system for identifying a reagent in which a compound crystallizes, comprising:
  (a) a robotic arm and a robotic arm controller which positions said robotic arm;
  (b) a system controller communicating with said robotic arm controller to control movement of said robotic arm, said system controller having a user interface for a user to design, schedule, optimize and/or monitor the operation of said system; and
  (c) an apparatus, under the control of said system controller, for introducing, storing and/or manipulating a matrix of reagents, wherein
     (i) the reagents collectively comprise a first type of precipitating agent which alters the activity coefficient of water, a second type of precipitating agent which increases the molecular crowding of a compound in solution, and a third type of precipitating agent which reduces the dielectric of a solution solvating the compound;

(ii) each reagent comprises two precipitating agents selected from the first, second and third type of precipitating agents, wherein the two precipitating agents are of a different type; and (iii) or each of the first, second and third types of precipitating agent, the matrix comprises at least two reagents differing from one another in that they comprise different species of, or different concentrations of, the type of precipitating agent.

Figure 1:
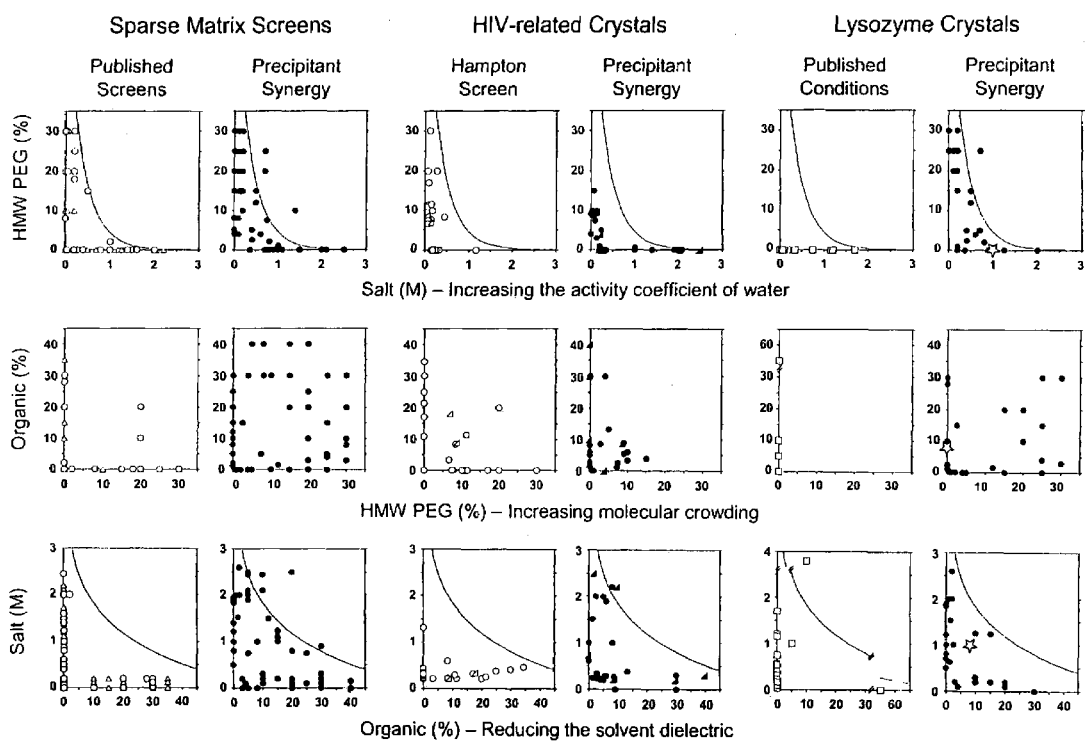
FIG. 1

Precipitant concentrations in commercial and PS reagent formulations, in HIV-envelope-related protein crystallization, and in hen egg-white lysozyme crystallizations. Precipitant concentrations are graphed with two-dimensional plots showing the concentrations of PEG versus salt (top six panels) concentrations of organic solvent versus PEG (middle six panels) and concentrations of salt versus organic solvent (bottom six panels). Insoluble regions are shown, as determined for PEG 4000 and $(NH_4)_2SO_4$ and for isopropanol and $(NH_4)_2SO_4$ (as taken from FIG. A 10.3 in [43]). All salts, PEGs and organic solvents are plotted on the same axes. A conversion factor between monovalent anions and divalent anions was determined by matching the solubility curves of the monovalent salt, NaCl, and the divalent salt, $(NH_4)_2SO_4$. A conversion factor of 1.6 (monovalent versus divalent salt) was used in the presence of organic solvents, and a conversion factor of 5.0 was used in the presence of PEG; molar concentrations of salts are plotted in divalent ion (or their equivalent) concentrations. Because this conversion only approximates the salt solubility and because different organics and PEGs behave differently, some of the PS conditions extend into the shaded "insoluble" region. The leftmost two columns show precipitant concentrations for the 146 reagent formulations of the Hampton crystal screen (○) and Wizard screens 1 and 2 (Δ) and for the 64 reagent formulations of the PS screen (•). The middle two columns show crystallization conditions for HIV-1-envelope-related proteins. Initial crystallization conditions are shown for the Hampton screen (○) and PS screen (•); optimized conditions are also shown as half squares for Hampton (⊿) and PS screen (◢) conditions. The rightmost two columns show lysozyme crystallization conditions, with previously published conditions in open squares (□) [44] and PS conditions in filled circles (•). The conditions that give rise to the C2 lysozyme crystals are highlighted with a star.

FIG. 2

Special position sulfate coordinates, hen egg-white lysozyme in space group C2. Hen egg-white lysozyme is depicted by an alpha-carbon (Cα) worm in dark grey, with symmetry related copy in lighter gray. Close to the dyad axis, all non-hydrogen atoms are shown. Each oxygen is coordinated by two hydrogen bonds: the topmost oxygens (closest to viewer) by H-bonds to the sidechain nitrogen (NE2) of Gln 121 and to a water molecule that bridges to the sidechain oxygen (OD1) of Asn 27. The sidechain nitrogen of Asn 27 (ND2) makes an H-bond to the bottom oxygen, which also makes an H-bond to the backbone nitrogen of Ser 24. Each of these hydrogen, bonds is preserved on the symmetry related molecule. A second sulfate ion is also present in the structure, and this can be seen half way between the termini, binding to a commonly used anion binding site composed of the sidechains of Arg 14 and His 15 [45, 46]. To aid in orienting the viewer, the amino- and carboxyl-termini of lysozyme have been labeled (N and C), and a small insert has been provided showing the entire lysozyme molecule. Figure made with GRASP [47].

DETAILED DESCRIPTION OF THE INVENTION

Definitions

"Am" shall mean an ammonium ion.

"Compound" shall include, without limitation, polypeptides, nucleic acids, glycomers, lipids and small molecules. In the preferred embodiment, the compound is a polypeptide.

"Contacting" a compound with a matrix of reagents shall mean immersing the compound in each reagent of the matrix so as to dissolve the compound in each reagent.

"Crystallize" shall mean, with respect to a compound, the transformation of that compound from its solvated form into its crystalline form.

"Glycomer" shall mean any carbohydrate-containing moiety. Glycomers include, without limitation, (a) complex carbohydrates, (b) polysaccharides, (c) oligosaccharides and (d) glycoconjugates. "Glycoconjugates" include, without limitation, glycoproteins, glycolipids and glycopolymers.

"Matrix of reagents" shall mean a plurality of reagents in separate compartments. In one embodiment, the reagents of such matrix are contained within a single apparatus. In another embodiment, the reagents are contained within a plurality of apparati. Apparati envisioned for this purpose include, without limitation, standard crystallization plates, and plates and scaffolds used in microassays and high through-put screening.

"Nucleic acid" shall mean a polymer of deoxyribonucleotides and/or ribonucleotides. The deoxyribonucleotides and ribonucleotides can be naturally occurring or synthetic analogues thereof.

"Organic compound" shall mean any carbon-containing compound. In one embodiment, the organic compound has a molecular weight of under 3000 Daltons. In another embodiment, the organic compound has a molecular weight of under 1000 Daltons. In a further embodiment, the organic compound has a molecular weight of under 500 Daltons.

"PEG" shall mean polyethylene glycol.

"Polypeptide" shall mean a polymer of amino acid residues. The amino acid residues can be naturally occurring or chemical analogues thereof. Polypeptides can also include modifications such as glycosylation, lipid attachment, sulfation, hydroxylation, and ADP-ribosylation.

"Reagent" shall mean a solution comprising precipitating agents as set forth in this application.

"Suitable period of time", with respect to identifying a reagent in which a compound has crystallized, shall mean any period of time within which crystallization might be expected to commence. Suitable periods of time include, without limitation, six hours, 12 hours, one day, two days, one week, two weeks, one month, two months, six months and one year.

EMBODIMENTS OF THE INVENTION

This invention provides a method for identifying a reagent in which a compound crystallizes, comprising the steps of:

(a) contacting the compound with a matrix of reagents, wherein
  (i) the reagents collectively comprise a first type of precipitating agent which alters the activity coefficient of water, a second type of precipitating agent which increases the molecular crowding of a compound in solution, and a third type of precipitating agent which reduces the dielectric of a solution solvating the compound;
  (ii) each reagent comprises two precipitating agents selected from the first, second and third type of precipitating agents, wherein the two precipitating agents are of a different type; and
  (iii) for each of the first, second and third types of precipitating agent, the matrix comprises at least two reagents differing from one another in that they comprise different species of, or different concentrations of, the type of precipitating agent; and
(b) after a suitable period of time, identifying one of the reagents, if any, in which the compound has crystallized, thereby identifying a reagent in which the compound crystallizes.

In one embodiment of the instant method, the compound is a polypeptide. The polypeptide can be, for example, a viral polypeptide, such as an HIV polypeptide. In another embodiment, the polypeptide of the instant method is associated with a disease.

In a further embodiment of the intstant method, the first type of precipitating agent is a salt. For example, the salt can be $Am_2SO_4$, NaCl, $NaKPO_4$, AmCitrate, $Li_2SO_4$ or NaFormate.

In a further embodiment of the instant method, the second type of precipitating agent is PEG. For example, the PEG can be PEG 3350, PEG 1500, PEG 8000 or PEG 4000.

In a further embodiment of the instant method, the third type of precipitating agent is an organic compound. For example, the organic compound can be PEG 400, glycerol, MPD or isopropanol.

In one embodiment of the instant method, the reagents have the same predetermined pH. For example, the pH of all reagents can be between about 4.5 to about 8.5.

In another embodiment of the instant method, the matrix comprises a plurality of groups of reagents, each group having one or more reagents, wherein each group of reagents has a different predetermined pH. For example, the matrix can comprise two groups of reagents, the first group having a pH between about 4.5 to about 6.5, and the second group having a pH between about 6.5 to about 8.5. In another example, the matrix comprises four groups, the first group having a pH between about 4.5 to about 5.5, the second group having a pH between about 5.5 to about 6.5, the third group having a pH between about 6.5 to about 7.5, and the fourth group having a pH between about 7.5 to about 8.5.

In another embodiment of the instant method, one or more reagents further comprises a salt selected from the group consisting of $MgSO_4$, $MgCl_2$, $CaCl_2$, $Li_2SO_4$, AmCitrate, $NaKPO_4$, $Am_2SO_4$ and NaCl.

In the instant method, the matrix can comprise any number of distinct reagents so long as it conforms to the requirements set forth herein. In one embodiment, the matrix comprises at least eight distinct reagents, at least 16 distinct reagents, at least 32 distinct reagents, at least 64 distinct reagents, at least 128 distinct reagents or at least 192 distinct reagents. In one specific example of the instant method, the matrix comprises the reagents as set forth in Table 1, 2 or 3.

The instant method can be performed manually or, in whole or in part, using an automated system.

It is stressed that the matrix used in the instant method ideally comprises additional precipitating agents, and a plurality of anions, cations, and buffers. Also, in this method, the compound can, but need not, already be known to crystallize in at least one reagent (which may or may not be included in the matrix). Specifically envisioned is the use of this method, and kits described below, to identify a crystallization reagent where no known such reagent has been identified, and also to identify a second or addition crystallization reagent where one or more known such reagents have been identified (e.g., "optimization" of a pre-determined reagent).

This invention further provides a method for crystallizing a compound comprising the steps of contacting the compound with a reagent for a suitable period of time, wherein the reagent has been identified, according to the instant methods, as a reagent in which the compound crystallizes.

This invention further provides a first kit for use in identifying a reagent in which a compound crystallizes, comprising a matrix of reagents wherein
  (i) the reagents collectively comprise a first type of precipitating agent which alters the activity coefficient of water, a second type of precipitating agent which increases the molecular crowding of a compound in solution, and a third type of precipitating agent which reduces the solvent dielectric of a solution solvating the compound;
  (ii) each reagent comprises two precipitating agents selected from the first, second and third type of precipitating agents, wherein the two precipitating agents are of a different type; and
  (iii) for each of the first, second and third types of precipitating agent, the matrix comprises at least two reagents differing from one another in that they comprise different species of, or different concentrations of, the type of precipitating agent.

In the preferred embodiment, the kit further comprises instructions for use.

In the instant kit, the matrix of reagents can be contained, for example, in (i) one or a plurality of well-containing plates suitable for use in growing crystals, whereby each reagent is contained within a discrete well, or (ii) a plurality of conical tubes suitable for use in growing crystals, whereby each tube contains a single reagent.

In one embodiment, the matrix of reagents is contained in one well-containing plate suitable for use in growing crystals. In another embodiment, the matrix of reagents is contained in a plurality of well-containing plates suitable for use in growing crystals. In the preferred embodiment, the well-containing plate(s) is suitable for use in an automated system. In another embodiment, the matrix of reagents is contained in a plurality of conical tubes suitable for use in growing crystals.

This invention further provides a second kit for use in identifying a reagent in which a compound crystallizes, which kit comprises a matrix of discrete combinations of agents, wherein
  (i) each discrete combination of agents, when combined with a predetermined amount of water, forms a reagent in which the agents are in solution at a predetermined concentration;
  (ii) the reagents, once formed, collectively comprise a first type of precipitating agent which alters the activity coefficient of water, a second type of precipitating agent which increases the molecular crowding of a compound in solution, and a third type of precipitating agent which reduces the solvent dielectric of a solution solvating the compound;

(iii) each reagent, once formed, comprises two precipitating agents selected from the first, second and third type of precipitating agents, wherein the two precipitating agents are of a different type; and (iv) once reagents are formed, for each of the first, second and third types of precipitating agent, the matrix comprises at least two reagents differing from one another in that they comprise different species of, or different concentrations of, the type of precipitating agent.

Finally, this invention provides an automated system for identifying a reagent in which a compound crystallizes, comprising:

(a) a robotic arm and a robotic arm controller which positions said robotic arm;

(b) a system controller communicating with said robotic arm controller to control movement of said robotic arm, said system controller having a user interface for a user to design, schedule, optimize and/or monitor the operation of said system; and (c) an apparatus, under the control of said system controller, for introducing, storing and/or manipulating a matrix of reagents, wherein (i) the reagents collectively comprise a first type of precipitating agent which alters the activity coefficient of water, a second type of precipitating agent which increases the molecular crowding of a compound in solution, and a third type of precipitating agent which reduces the dielectric of a solution solvating the compound;

(ii) each reagent comprises two precipitating agents selected from the first, second and third type of precipitating agents, wherein the two precipitating agents are of a different type; and (iii) or each of the first, second and third types of precipitating agent, the matrix comprises at least two reagents differing from one another in that they comprise different species of, or different concentrations of, the type of precipitating agent.

In one embodiment, the instant automated system, further comprises:

(a) an apparatus, under the control of said system controller, for contacting a compound with the matrix of reagents; and/or (b) an apparatus, under the control of said system controller, for identifying the presence of a crystal in a reagent with which a compound has be contacted.

It is noted that each of the various embodiments set forth above with respect to the instant method for identifying a reagent in which a compound crystallizes also applies, *mutatis mutandis*, to each of the instant method for crystallizing a compound, kit and automated system.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Intoduction

In this work, the effect of explicitly treating each mechanistically distinct class of precipitating agent as an independent factor is explored. The results show that rigorous analysis of the independent factors that provide the orthogonal basis of the sparse matrix can significantly and unexpectedly increase the overall probability of crystallization as well as the quality of the final optimized crystals.

Summary

Suitable conditions for protein crystallization are commonly identified by screening combinations of independent factors that affect crystal formation. Because precipitating agents are prime determinants of crystallization, it was investigated whether a systematic exploration of combinations of mechanistically distinct precipitants would enhance crystallization. A crystallization screen containing 64 precipitant mixtures was devised. Tests with ten HIV-envelope-related proteins demonstrated that use of precipitant mixtures significantly enhanced both the probability of crystallization as well as the quality of optimized crystals. Tests with hen egg-white lysozyme generated a novel C2 crystal from a salt/organic solvent mixture; structure solution at 2 Å resolution revealed a lattice held together by both hydrophobic and electrostatic dyad-interactions. The results indicate that mechanistically distinct precipitants can synergize, with precipitant combinations adding unique dimensions to protein crystallization.

Results and Discussion

Precipitant Synergy (PS) screen

Precipitants that function by different mechanisms show little exchangeability. Crystals obtained with one type of precipitant (e.g. high salt) do not commonly form if the precipitant is replaced by a functionally different one (e.g. PEG or an organic solvent). In addition, a significant number of crystallizations have been reported using combinations of mechanistically distinct precipitants, many of which could not be obtained with single precipitants [13-19].

To test the hypothesis that the relative probability of obtaining crystals with precipitant combinations is high and that such conditions are not replicated in other regions of crystallization space, a screen that sampled combinations of mechanistically distinct precipitating agents was devised (Table 1). The screen used five independent variables/dimensions: three different precipitating agents, pH, and the presence of an additive (generally a divalent salt) Within each independent variable, several steps were used (five pH values, eight salt precipitants, four high molecular weight PEGs, four different solvents, and nine different additives). Sampling was balanced in pH and in overall coverage of 2-precipitant mixtures.

High molecular weight PEG/organic solvent mixtures were miscible at all concentrations used in the screen (FIG. 1). However, many of the other precipitant combinations were inaccessible. High salt combinations with either organic solvents or with high molecular weight PEGs resulted in phase separations or salt crystallization. With salts at divalent ionic strengths of 2-3 M, greater than 99% of potential mixtures with PEG (0 to 35%) were insoluble, and greater than 80% of potential mixtures with organic solvents (0 to 45%) were insoluble (FIG. 1). Even fewer triple salt/PEG/organic conditions were accessible. Despite these limitations, 67% of the 2-precipitant crystallization space could be tested (to 2 M divalent ion strength, 30% PEG and 40% organic solvent). In addition, the combinations often lowered the precipitation point of the test proteins to a point at which precipitant combinations could be evaluated. For example, the addition of 10% MPD reduced the precipitation point of Fab 17b in $Li_2SO_4$ from above saturation (greater than 2.8 M $Li_2SO_4$) to 1.9 M $Li_2SO_4$, within the solubility limit of the $Li_2SO_4$/MPD mixture.

Reagents similar to those used in standard commercial screens were chosen (Hampton Research and Emerald BioStructures) to permit greater ease in comparison, although alternatives may yield higher probabilites of crystallization. For example, sodium malonate has been shown to be much more effective than other salts in crystallizing macromolecules [20], and crystallization conditions for protein-protein complexes heavily favor PEG conditions [21]. In addition, other precipitants may provide better access to "insoluble" regions of precipitant space. Poly(acrylic acid), which has been successfully used in crystallizing biomolecules, was tested [22]. It was found that 30% (w/v) poly (acrylic acid sodium salt) of 2.1 kDa and 5.1 kDa was soluble at up to 3.2 M and 2.8 M $Am_2SO_4$, respectively. The use of poly(acrylic acid) or other charged polymers would be expected to permit access to the molecular crowding/high ionic strength regions of crystallization space inaccessible to the PEG used here.

Precipitant concentrations in the PS reagents were set "high" so that most of the test proteins precipitated when combined in a 1:1 ratio. The rationale for using such high levels of precipitant is that when probing for the precipitation point, it is operationally much easier to dilute a pre-formulated reagent than it is to increase the precipitant, especially with a precipitant mixture. Most of the crystals that were ultimately obtained in the PS screen used greater than 2-fold dilutions of the reagent formulations given in Table 1.

Comparison of Precipitant Synergy (PS) and Previously Published Crystal Screens

The precipitant crystallization space covered by the Hampton crystal screen (Hampton Research) and Wizard 1 and Wizard 2 screens (Emerald BioStructures) focused on the precipitant axes (FIG. 1). In contrast, the precipitant synergy (PS) screen that was devised covered most of the accessible crystallization space. With PEG/organic mixtures, the 146 conditions of the Hampton and Wizard commercial screens contained 2 PEG/organic mixtures, whereas the 64 conditions of the PS screen contained 31 PEG/organic mixtures, sampling on average 5% intervals in PEG and 8% intervals in organic solvent. Slightly more coverage was observed in the commercial screens for PEG/salt and organic/salt mixtures. Nonetheless, the PS screen covered a greater area of precipitant crystallization space, with a greater density of sampling.

To compare the relative probability of success for the Hampton and PS screens, ten HIV-envelope-related proteins and protein complexes were tested and included data that had been previously compiled on 4-domain human CD4 [16] (Table 2). It was observed earlier that crystals of 4-domain human CD4 grew in salt/PEG mixtures [16]. The HIV-envelope-related proteins were chosen because they are notoriously difficult to crystallize, with HIV-envelope flexibility as well as unusually long complementarity-determining-loops on HIV-envelope-neutralizing antibodies inhibiting crystallization [23, 24].

While the number of conditions producing initial crystals was similar for both screens, the number of different space groups was 2-fold greater with the PS screen than with the Hampton screen, and the number of crystals suitable for structural analysis was 3-fold greater (Table 2).

A second test of the utility of the PS screen is the combination of screen results (Hampton+PS) for different space groups and for those suitable for structural analysis. In both cases, the combined Hampton+PS numbers were greater than either the Hampton or PS screen alone. A 3.5-fold increase in the number of crystals suitable for structural analysis was observed in the Hampton+PS verses the Hampton alone, compared to only a 1.1-fold increase in the Hampton+PS verses the PS alone (Table 2). In three cases where no crystals were obtained in the Hampton screen, crystals suitable for structural analysis were obtained in the PS screen. The results indicate that the PS screen contains conditions not sampled by the Hampton screen, and moreover, that the sampling of these conditions greatly increases the overall probability of crystallization. While additional crystals can always be grown by increasing the number of crystallization trials, many crystallizations using single precipitants screens appear to sample similar regions of crystallization space. It is noted that screening over 1000 additional conditions for 4-domain CD4, did not yield additional crystals (unpublished observations].

Many of the conditions that generated suitable crystals in the Hampton screen actually involved precipitant combinations. For example, one HIV-envelope complex yielded crystals suitable for structural analysis in the Hampton, but not the PS screen (17b/D1D2/YU2 gp120; Table 4). However, upon optimization (see below), crystals grew best in a precipitant mixture of 7% PEG 8000 and 18% ethanol (Table 5) [25].

Optimization of Initial HIV-Envelope-Related Protein Crystals: use of "Local Sparse Matrix"

The initial crystals obtained in the Hampton and PS sparse matrix screens were optimized using a three step procedure: first a precipitant: protein concentration matrix was tested, to generate a rough idea of the crystalline reproducibility and the optimal precipitant: protein concentration mixture. Second, a "local sparse matrix" was used to uncover optimization leads. This "local sparse matrix" combined 90% of each crystallization condition identified in step (1) with 10% of each Hampton crystal screen solution, creating a constrained sparse matrix around each crystallization point (care was taken with these mixtures to avoid insoluble salt combinations, for example, combining calcium and phosphate). If suitable crystals for structural analysis could not be obtained by further standard additive or single variable optimization, a third optimization step was employed. This third step screened "equivalent" regions of precipitant space. For example, if crystals were initially identified in mixtures of high salt (or high PEG concentrations) with low organic solvent, "equivalent" mixtures of high organic solvent with low salt (or low PEG concentrations) were tested.

This 3-step optimization procedure generated the 16 crystals described in Table 5. All 16 grew best in precipitant mixtures. While some of these mixtures required minor quantities of a second precipitant, the secondary components often pushed the precipitant combination to near the precipitant mixture solubility limit. For example, the presence of 2.5% PEG 400, brought 2 M $Am_2SO_4$ close to the $Am_2SO_4$: PEG 400 solubility limits. Screening the "phase equivalent" $Am_2SO_4$: PEG 400 at 30-40% PEG 400, identified additional crystal forms [16]. In addition to these minor component mixtures, many of the other crystallizations contained high percentages of at least two mechanistically distinct precipitants.

Since crystals can obviously grow from single precipitants, it is striking that all 16 that were good enough for space group determination grew from precipitant mixtures. One explanation is that since mechanistically distinct precipitants are independent crystallization factors, one would expect each to have a different crystallization optimum.

Thus for example, if one carried out a sparse matrix fixing the pH of all conditions at 7.0, it would not be surprising that upon optimization, most of the crystals that had been initially identified at pH 7.0, would grow optimally at a different pH. The fact that the HIV-envelope-related proteins have a relatively low success rate of crystallization may magnify the need to fully optimize each independent crystallization parameter; for the 11 HIV-envelope-related proteins, each tested in 114 conditions, only 7 crystals were obtained suitable for structural analysis, giving a success rate of 7/(11*114) or 0.0056, whereas with hen egg-white lysozyme, almost 50% of the PS conditions gave useful crystals (see below).

Tests with Hen Egg-White Lysozyme

Another way to analyze the utility of the PS screen is by examining its effect on an extremely well studied protein like hen egg-white lysozyme. A number of different space groups have been reported [26-30], obtained primarily through variations in the anions and cations used for crystallization. A summary of the published crystallization conditions for hen egg-white lysozyme is shown in FIG. 1.

In the PS screen, 29 out of 64 conditions were able to support lysozyme crystals, virtually all of which turned out to be tetragonal ($P4_32_12$). Despite this commonality, a novel C2 lattice, never previously reported, grew in PS condition 17 from a $Li_2SO_4$/MPD mixture. The crystal had cell dimension: a=42.94 Å, b=53.14 Å, c=50.21 Å, and β=97.32°, and diffracted to Bragg spacings of better than 2 Å resolution.

Figure 2:
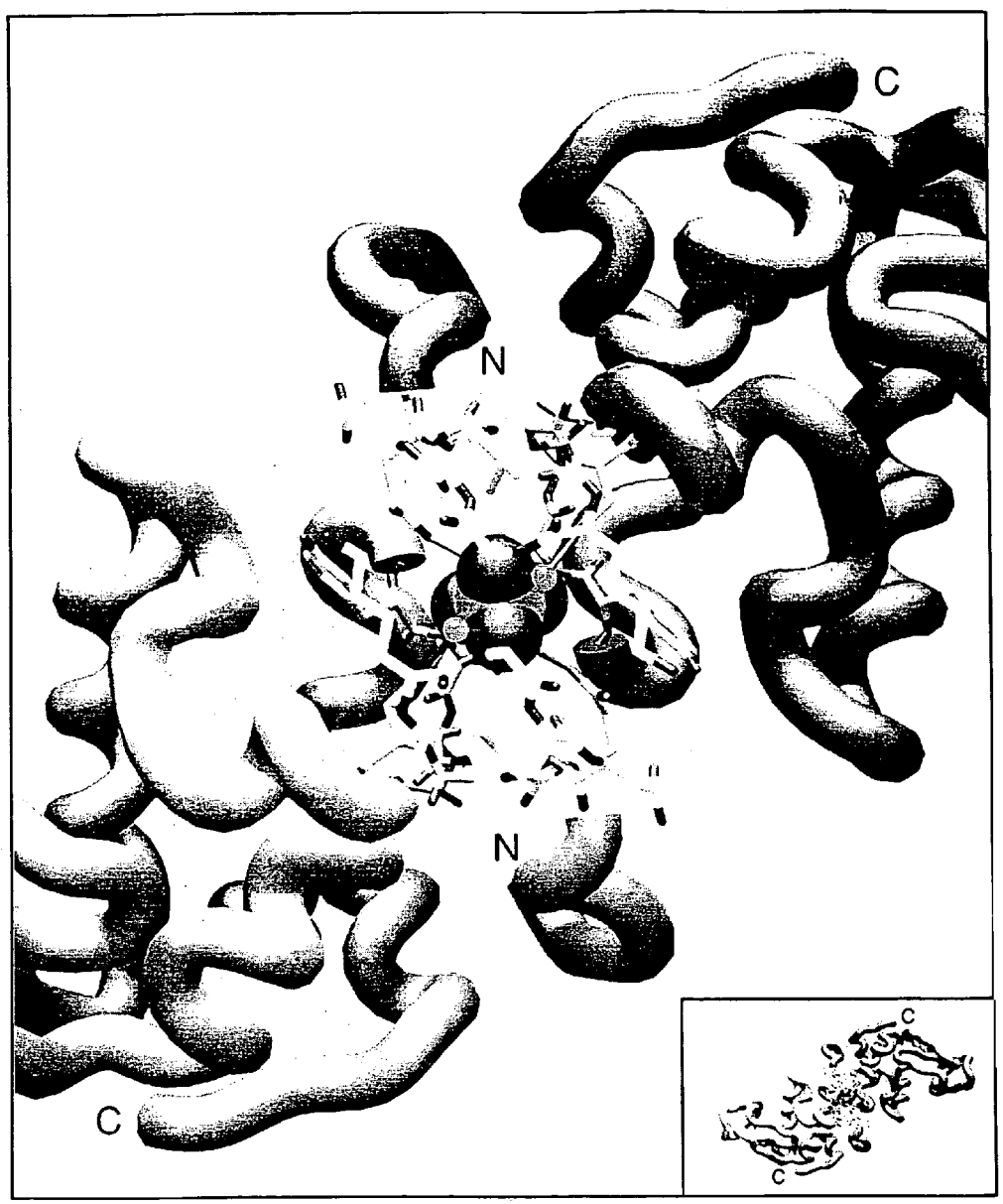

Structure solution by molecular replacement and refinement to an R-factor of 18.9% (500-2.0 Å; $R_{free}$=25.0%; all data >0σ) revealed a lattice held together by a sulfate ion coordinating two lysozyme molecules about a crystallographic dyad (FIG. 2). A striking hydrophobic interaction involving the indole ring of Trp 62 stacking against a symmetry related copy of itself was observed about a parallel dyad (C2 contains two unique dyads at c=0 and c=½). Both of these dyad interactions had not been previously observed for lysozyme. It is tempting to speculate that the mixture of electrostatic interactions (stabilized by organic solvent precipitants) and hydrophobic interactions (facilitated by high salt), which hold together this C2 lattice, may reflect the mixture of organic solvent/high salt precipitants used in the crystallization. However, the predominance of tetragonal lysozyme crystals in many different mixtures indicates that the determinants of polymorphism are complex. Nonetheless, crystal formation may proceed from only a small number of lattice contacts [31]. The ability of precipitant mixtures to simultaneously stabilize different types of protein interactions may account in part for their capacity to enhance the overall probability of crystallization.

Independent Variables and Sparse Matrix Screening

In devising a sparse matrix screen, the choice of independent factors that define the matrix as well as the density and balance of the sampling are of importance [32]. Omitting factors or not treating independent factors as separate variables results in loss of sampling for large regions of crystallization space. At the other extreme, treating highly dependent factors as independent variables results in oversampling of select regions. The step size of any particular variable is of lesser importance, as long as the matrix is appropriately balanced and the step size is within the tolerances of crystallization. An additional consideration is that the relative probability of crystallization in each sampled region of crystallization space has an influence on the overall probability of the sparse matrix screen.

Precipitants have complex effects on proteins. For example, MPD affects both the solvent dielectric and the activity coefficient of water [33]. Nonetheless, it is possible to classify these effects operationally in that precipitants from the same class exhibit correlative solubilities and can often substitute for each other, whereas precipitants that function by different mechanisms do not and cannot. Thus, for example, since MPD and PEG 400 exhibit correlative solubilities and can often substitute for organic solvents, but rarely for high salts or higher molecular weight polymers, they were operationally classified as organic solvents.

Several 2-precipitant mixtures have been analyzed by grid screening (e.g. Hampton Research offers PEG 6,000 screens with LiCl or $(NH_4)_2SO_4$). While such grid screening incorporates some of the benefits of precipitant synergy, grid screening lacks the multivariate advantages of the sparse matrix approach [34, 35]. The dependence of the C2 lysozyme crystallization not only on the presence of high salt and organic solvent precipitants, but also on the presence of a particular divalent anion (sulfate) demonstrates the multidimensional requirements of protein crystallization. Indeed, it was found that similar crystals could also be grown in PS condition 29 when spiked with sodium (unpublished observations). PS condition 29 contains a PEG/MPD precipitant mixture and only has sulfate as an additive.

The results suggest that the independent factors that form the orthogonal basis for a sparse crystallization matrix should encompass anions, cations, additives (e.g. small amphiphiles, multivalent salts, or detergents [36]), the standard crystallization variables (temperature and pH) as well as the three classes of mechanistically distinct precipitants (salt, PEG and organic solvent), which were focused on here. Even if only 4 steps were permitted for each of these 8 independent factors, a full grid search would require placing the protein at the precipitation point for 48 or 65,536 conditions. Though screening such a multitude of conditions seems unfeasible, robots have been developed that test crystallization conditions using only ~0.05 μl droplets [37]. In addition, the use of an average sampling distance of 1.5 steps would reduce testing to only 1 in 26 conditions within the 8-dimensional grid, and correlation of protein solubility should allow precipitation points to be achieved with 2-3 droplets for each condition sampled. These considerations suggest that with existing robotic technology, an 8-dimensional, 4-step, sparse matrix could be screened with as little as 1.5 mg of a 5 mg/ml protein solution.

Operationally, mechanistically distinct precipitants act as independent crystallization factors. The consideration of additional factors exponentially increases the number of crystallization conditions that should be sampled. Tests with a few difficult-to-crystallize proteins using a relatively limited 64-condition "PS screen" showed a significant increase in the overall probability of crystallization. Because of industrial scale applications of protein crystallography, for example to structural genomics, even a 2-fold increase in the average probability of crystallization should have substantial practical impact. At the individual protein-level, the growth of a novel form of hen egg-white lysozyme, despite this protein's extensive characterization, demonstrates the remarkable crystallization synergy of precipitant mixtures.

EXPERIMENTAL PROCEDURES

Crystallization Studies with HIV-Related Proteins

Antigen-binding fragments (Fabs) and complexes of HIV-related proteins were prepared as described previously [23, 25]. Proteins (5-10 mg/ml in 350 mM NaCl, 2.5 mM Tris pH 7.1, 0.02% NaN$_3$) were screened for crystallization using the hanging droplet method: 0.5 μl of protein was combined with 0.5 μl reservoir and placed over a 200-1500 μl reservoir (reservoir size varied as precipitant concentration was adjusted). NaCl was added to the reservoir after the droplet was set up to normalize for the 350 mM salt in the protein solution. Optimally, screening requires placing each protein at its precipitation point, which were accomplished by diluting/increasing the precipitant in each condition. Screening was initially carried out with the Crystal Screen (Hampton Research), since the predominance of its single precipitant conditions made correlation of precipitation behavior more straightforward. Ten Hampton conditions (4, 8, 14, 17, 18, 20, 21, 33, 39, 40) were chosen and the protein was placed at the precipitation point for each of these using binomial optimization. This usually required 4-5 crystallization trials for each condition. Results from these 10 initial conditions allowed precipitation points to be extrapolated for the remaining 40 Hampton conditions. These were set up using two droplets: one below and one at the predicted precipitation point, with optimizations performed as required. From the observed solubility in the Hampton screen, the precipitation points for 10 PS screen conditions (2, 11, 13, 14, 22, 30, 34, 47, 56, 64) were predicted and crystallizations set up. The remaining 54 PS conditions were then set up at precipitation points extrapolated from the observed solubilities. Optimizations were carried out as required. All crystallizations were set up at 20° C. If no crystals were observed after two months, crystallization trays were transferred to 4° C. and reviewed periodically for crystal growth.

Hen Egg-White Lysozyme 3x-crystallized hen egg-white lysozyme (Sigma) was dissolved in water to a concentration of 20 mg/ml. Hanging droplets (1.0 μl protein with 1.0 μl reservoir) were used for screening as described above except that an additional seeding step was added to ensure that all conditions capable of growing the common tetragonal form of lysozyme were identified. Initial crystals of C2 lysozyme grew in 100% of PS condition 17 after the droplet had equilibrated for over two months. Crystals appeared more rapidly if after setting up the droplet, the reservoir (200 μl PS condition 17) was spiced with 20 μl MPD and 100 μl 5 M NaCl. Data were collected on Paratone-N flash-cooled crystals, and processed with Denzo/Scalepack [38]. The structure of lysozyme in C2 was solved with AMoRe [39] using PDB accession code liee [40], and refined with X-PLOR [41] and CNS [42]. Because these refinement programs do not allow molecular bonding with special position atoms, the refinement was initially carried out in space group C1 (with one special position sulfate and two lysozyme molecules in the asymmetric unit). The C1 refinement converged with the sulfur atom of the special position sulfate placed precisely on the crystallographic dyad, and the sulfate oxygens positioned to within 0.02 Å of their C2 dyad symmetry mates. The positions of the sulfate oxygens were averaged to assume perfect C2 symmetry, the entire sulfate fixed, and the structure refined in C2 (with lattice symmetry generating two of the four sulfate oxygens about the crystallographic dyad).

TABLE 1

Precipitant Synergy (PS) Reagent Formulation

| | Mechanism to enhance protein association | | | | |
|---|---|---|---|---|---|
| Reagent | (Salt) Alter the activity coefficient of water | (PEG) Increase molecular crowding | (Organic) Reduce the solvent dielectric | pH | Additive |
| 1 | 2M Am$_2$SO$_4$ | | 2% PEG 400 | 5.5 | |
| 2 | 2M Am$_2$SO$_4$ | | 10% Glycerol | 6.5 | 0.1M MgSO$_4$ |
| 3 | 2M Am$_2$SO$_4$ | | 1% MPD | 7.5 | |
| 4 | 2M Am$_2$SO$_4$ | | 5% PEG 400 | 8.5 | 0.1M MgSO$_4$ |
| 5 | 4M NaCl | | 2% PEG 400 | 5.5 | 0.1M MgCl$_2$ |
| 6 | 3M NaCl | | 5% MPD | 6.5 | 0.1M CaCl$_2$ |
| 7 | 4M NaCl | | 5% Isopropanol | 7.5 | |
| 8 | 2.5M NaKPO$_4$ | | 5% Isopropanol | 5.5 | |
| 9 | 2M NaKPO$_4$ | | 2% PEG 400 | 6.5 | |
| 10 | 2.5M NaKPO$_4$ | | 20% Glycerol | 7.5 | |
| 11 | 1M NaKPO$_4$ | | 8% MPD | 8.5 | |
| 12 | 2M AmCitrate | | 1% MPD | 4.5 | |
| 13 | 2M AmCitrate | | 5% Isopropanol | 6.5 | |
| 14 | 2M AmCitrate | | 5% PEG 400 | 7.5 | |
| 15 | 2M LiSO$_4$ | | 5% Isopropanol | 4.5 | 0.1M MgSO$_4$ |
| 16 | 2M LiSO$_4$ | | 5% PEG 400 | 5.5 | 0.1M MgSO$_4$ |
| 17 | 2M LiSO$_4$ | | 8% MPD | 6.5 | |
| 18 | 2M LiSO$_4$ | | 2% PEG 400 | 8.5 | |
| 19 | 1M LiSO$_4$ | | 15% MPD | 4.5 | 0.1M MgSO$_4$ |
| 20 | 0.75M AmCitrate | | 25% MPD | 5.5 | |
| 21 | 1.5M Am$_2$SO$_4$ | | 12% Isopropanol | 6.5 | |
| 22 | 1.3M NaCl | | 30% Isopropanol | 6.5 | 0.1M CaCl$_2$ |
| 23 | 4M NaCl | | 10% PEG 400 | 7.5 | |
| 24 | 0.8M NaKPO$_4$ | | 20% PEG 400 | 7.5 | |
| 25 | 1M AmCitrate | | 15% Isopropanol | 8.5 | |
| 26 | 2M NaFormate | 2.5% PEG 3350 | 15% Isopropanol | 8.5 | |
| 27 | | 25% PEG 1500 | 30% MPD | 4.5 | |
| 28 | | 15% PEG 8000 | 30% MPD | 5.5 | 0.1M CaCl$_2$ |
| 29 | | 10% PEG 3350 | 30% MPD | 6.5 | 0.2M Am$_2$SO$_4$ |
| 30 | | 4% PEG 1500 | 30% MPD | 7.5 | |
| 31 | | 8% PEG 8000 | 30% MPD | 8.5 | 0.5M NaCl |
| 32 | | 4% PEG 3350 | 30% Isopropanol | 4.5 | 0.1M CaCl$_2$ |
| 33 | | 10% PEG 1500 | 30% Isopropanol | 5.5 | 0.2M LiSO$_4$ |

TABLE 1-continued

Precipitant Synergy (PS) Reagent Formulation

Mechanism to enhance protein association

| Reagent | (Salt) Alter the activity coefficient of water | (PEG) Increase molecular crowding | (Organic) Reduce the solvent dielectric | pH | Additive |
|---|---|---|---|---|---|
| 34 | | 15% PEG 8000 | 40% Isopropanol | 6.5 | |
| 35 | | 15% PEG 3350 | 20% Isopropanol | 7.5 | 0.2M AmCitrate |
| 36 | | 30% PEG 3350 | 30% Isopropanol | 8.5 | |
| 37 | | 20% PEG 8000 | 40% PEG 400 | 4.5 | |
| 38 | | 5% PEG 3350 | 40% PEG 400 | 5.5 | |
| 39 | | 15% PEG 1000 | 40% PEG 400 | 6.5 | 0.15M NaKPO$_4$ |
| 40 | | 8% PEG 8000 | 40% PEG 400 | 7.5 | |
| 41 | | 20% PEG 3350 | 25% PEG 400 | 8.5 | 0.1M MgCl$_2$ |
| 42 | | 30% PEG 1500 | 3% MPD | 5.5 | 0.2M MgSO$_4$ |
| 43 | | 30% PEG 1500 | 10% Isopropanol | 6.5 | 0.1M CaCl$_2$ |
| 44 | | 30% PEG 1500 | 20% PEG 400 | 7.5 | |
| 45 | | 30% PEG 1500 | 8% MPD | 8.5 | |
| 46 | | 25% PEG 3350 | 15% Isopropanol | 4.5 | 0.2M AmCitrate |
| 47 | | 25% PEG 3350 | 5% PEG 400 | 5.5 | |
| 48 | | 25% PEG 3350 | 15% MPD | 6.5 | 0.2M LiSO$_4$ |
| 49 | | 25% PEG 3350 | 4% Isopropanol | 7.5 | 0.1M CaCl$_2$ |
| 50 | | 20% PEG 8000 | 10% PEG 400 | 5.5 | 0.5M NaCl |
| 51 | | 20% PEG 8000 | 3% MPD | 6.5 | |
| 52 | | 20% PEG 8000 | 10% Isopropanol | 7.5 | 0.2M Am$_2$SO$_4$ |
| 53 | | 20% PEG 8000 | 20% PEG 400 | 8.5 | 0.1M MgCl$_2$ |
| 54 | 3M NaFormate | 25% PEG 3350 | | 4.5 | 0.1M CaCl$_2$ |
| 55 | 0.75M Am$_2$SO$_4$ | 7.5% PEG 3350 | 5% Isopropanol | 4.5 | |
| 56 | 1M AmCitrate | 1% PEG 4000 | | 5.5 | |
| 57 | 2.5M NaCl | 12% PEG 1500 | 1.5% MPD | 5.5 | |
| 58 | 3M NaCl | 20% PEG 3350 | | 6.5 | 0.1M MgCl$_2$ |
| 59 | 3M NaFormate | 4% PEG 8000 | | 6.5 | |
| 60 | 1M NaKPO$_4$ | 0.5% PEG 4000 | | 7.5 | |
| 61 | 1.4M NaKPO$_4$ | 10% PEG 3350 | | 7.5 | |
| 62 | 0.8M AmCitrate | 2% PEG 8000 | | 8.5 | |
| 63 | 2M NaCl | 5% PEG 4000 | | 8.5 | |
| 64 | 0.5M AmCitrate | 5% PEG 8000 | | 8.5 | |

TABLE 2

| Well/Reagent | Compound Buffer | Precipitant | Additive |
|---|---|---|---|
| 1 | 100.000 mM NaAc/acetic acid pH: 5.5 | 2000.000 mM (NH4)2 sulfate 2.000% v/v PEG-400 | |
| 2 | 100.000 mM imidazole/HCl pH: 6.5 | 2000.000 mM (NH4)2 sulfate 10.000% v/v glycerol | 100.000 mM magnesium sulfate |
| 3 | 100.000 mM HEPES/NaOH pH: 7.5 | 1.000% v/v MPD 2000.000 mM (NH4)2 sulfate | |
| 4 | 100.000 mM Tris base/HCl pH: 8.5 | 2000.000 mM (NH4)2 sulfate 5.000% v/v PEG-400 | 100.000 mM magnesium sulfate |
| 5 | 100.000 mM NaAc/acetic acid pH: 5.5 | 3900.000 mM NaCl 2.000% v/v PEG-400 | 100.000 mM MgCl2 |
| 6 | 100.000 mM imidazole/HCl pH: 6.5 | 5.000% v/v MPD 3000.000 mM NaCl | 100.000 mM CaCl2 |
| 7 | 100.000 mM HEPES/NaOH pH: 7.5 | 4000.000 mM NaCl 5.000% v/v isopropanol | |
| 8 | 2500.000 mM K2H phosphate/NaH2 phosphate pH: 5.5 | 5.000% v/v isopropanol | |
| 9 | 2000.000 mM K2H phosphate/NaH2 phosphate pH: 6.5 | 2.000% v/v PEG-400 | |
| 10 | 2500.000 mM K2H phosphate/NaH2 phosphate pH: 7.5 | 20.000% v/v glycerol | |
| 11 | 1000.000 mM K2H phosphate/NaH2 phosphate pH: 8.5 | 8.000% v/v MPD | |
| 12 | 2000.000 mM (NH4)3 citrate/citric acid pH: 4.5 | 1.000% v/v MPD | |
| 13 | 2000.000 mM (NH4)3 citrate/citric acid pH: 6.5. | 5.000% v/v isopropanol | |
| 14 | 2000.000 mM (NH4)3 citrate/citric acid pH: 7.5 | 5.000% v/v PEG-400 | |
| 15 | 100.000 mM NaAc/acetic acid pH: 4.5 | 5.000% v/v isopropanol 2000.000 mM Li2 sulfate | 100.000 mM magnesium sulfate |
| 16 | 100.000 mM NaAc/acetic acid pH: 5.5 | 2000.000 mM Li2 sulfate 5.000% v/v PEG-400 | 100.000 mM magnesium sulfate |
| 17 | 100.000 mM imidazole/HCl pH: 6.5 | 2000.000 mM Li2 sulfate 8.000% v/v MPD | |

TABLE 2-continued

| Well/Reagent | Compound Buffer | Precipitant | Additive |
|---|---|---|---|
| 18 | 100.000 mM Tris base/HCl pH: 8.5 | 2000.000 mM Li2 sulfate 2.000% v/v PEG-400 | |
| 19 | 100.000 mM NaAc/acetic acid pH: 4.5 | 15.000% v/v MPD 1000.000 mM Li2 sulfate | 100.000 mM magnesium sulfate |
| 20 | 750.000 mM (NH4)3 citrate/citric acid pH: 5.5 | 25.000% v/v MPD | |
| 21 | 100.000 mM imidazole/HCl pH: 6.5 | 1500.000 mM (NH4)2 sulfate 12.000% v/v isopropanol | |
| 22 | 100.000 mM imidazole/HCl pH: 6.5 | 30.000% v/v isopropanol 1300.000 mM NaCl | 100.000 mM CaCl2 |
| 23 | 100.000 mM HEPES/NaOH pH: 7.5 | 4000.000 mM NaCl 10.000% v/v PEG-400 | |
| 24 | 800.000 mM K2H phosphate/NaH2 phosphate pH: 7.5 | 20.000% v/v PEG-400 | |
| 25 | 1000.000 mM (NH4)3 citrate/ammonium hydroxide pH: 8.5 | 15.000% v/v isopropanol | |
| 26 | 100.000 mM Tris base/HCl pH: 8.5 | 15.000% v/v isopropanol 2.500% w/v PEG-3350 2000.000 mM Sodium formate | |
| 27 | 100.000 mM NaAc/acetic acid pH: 4.5 | 30.000% v/v MPD 25.000% w/v PEG 1500 | |
| 28 | 100.000 mM NaAc/acetic acid pH: 5.5 | 30.000% v/v MPD 15.000% w/v PEG-8000 | 100.000 mM CaCl2 |
| 29 | 100.000 mM imidazole/HCl pH: 6.5 | 30.000% v/v MPD 10.000% w/v PEG-3350 | 200.000 mM (NH4)2 sulfate |
| 30 | 100.000 mM HEPES/NaOH pH: 7.5 | 30.000% v/v MPD 4.000% w/v PEG 1500 | |
| 31 | 100.000 mM Tris base/HCl pH: 8.5 | 30.000% v/v MPD 8.000% w/v PEG-8000 | 500.000 mM NaCl |
| 32 | 100.000 mM NaAc/acetic acid pH: 4.5 | 30.000% v/v isopropanol 4.000% w/v PEG-3350 | 100.000 mM CaCl2 |
| 33 | 100.000 mM NaAc/acetic acid pH: 5.5 | 10.000% w/v PEG 1500 30.000% v/v isopropanol | 200.000 mM Li2 sulfate |
| 34 | 100.000 mM imidazole/HCl pH: 6.5 | 15.000% w/v PEG-8000 40.000% v/v isopropanol | |
| 35 | 200.000 mM (NH4)3 citrate/citric acid pH: 7.5 | 20.000% v/v isopropanol 15.000% w/v PEG-3350 | |
| 36 | 100.000 mM Tris base/HCl pH: 8.5 | 30.000% v/v isopropanol 30.000% w/v PEG-3350 | |
| 37 | 100.000 mM NaAc/acetic acid pH: 4.5 | 20.000% w/v PEG-8000 40.000% v/v PEG-400 | |
| 38 | 100.000 mM NaAc/acetic acid pH: 5.5 | 40.000% v/v PEG-400 5.000% w/v PEG-3350 | |
| 39 | 150.000 mM K2H phosphate/NaH2 phosphate pH: 6.5 | 15.000% v/v PEG 1000 40.000% v/v PEG-400 | |
| 40 | 100.000 mM HEPES/NaOH pH: 7.5 | 8.000% w/v PEG-8000 40.000% v/v PEG-400 | |
| 41 | 100.000 mM Tris base/HCl pH: 8.5 | 25.000% v/v PEG-400 20.000% w/v PEG-3350 | 100.000 mM MgCl2 |
| 42 | 100.000 mM NaAc/acetic acid pH: 5.5 | 3.000% v/v MPD 30.000% w/v PEG 1500 | 200.000 mM magnesium sulfate |
| 43 | 100.000 mM imidazole/HCl pH: 6.5 | 30.000% w/v PEG 1500 10.000% v/v isopropanol | 100.000 mM CaCl2 |
| 44 | 100.000 mM HEPES/NaOH pH: 7.5 | 30.000% w/v PEG 1500 20.000% v/v PEG-400 | |
| 45 | 100.000 mM Tris base/HCl pH: 8.5 | 8.000% v/v MPD 30.000% w/v PEG 1500 | |
| 46 | 200.000 mM (NH4)3 citrate/citric acid pH: 4.5 | 15.000% v/v isopropanol 25.000% w/v PEG-3350 | |
| 47 | 100.000 mM NaAc/acetic acid pH: 5.5 | 5.000% v/v PEG-400 25.000% w/v PEG-3350 | |
| 48 | 100.000 mM imidazole/HCl pH: 6.5 | 15.000% v/v MPD 25.000% w/v PEG-3350 | 200.000 mM Li2 sulfate |
| 49 | 100.000 mM HEPES/NaOH pH: 7.5 | 25.000% w/v PEG-3350 4.000% v/v isopropanol | 100.000 mM CaCl2 |
| 50 | 100.000 mM NaAc/acetic acid pH: 5.5 | 20.000% w/v PEG-8000 10.000% v/v PEG-400 | 500.000 mM NaCl |
| 51 | 100.000 mM imidazole/HCl pH: 6.5 | 3.000% v/v MPD 20.000% w/v PEG-8000 | |
| 52 | 100.000 mM HEPES/NaOH pH: 7.5 | 20.000% w/v PEG-8000 10.000% v/v isopropanol | 200.000 mM (NH4)2 sulfate |
| 53 | 100.000 mM Tris base/HCl pH: 8.5 | 20.000% w/v PEG-8000 20.000% v/v PEG-400 | 100.000 mM MgCl2 |
| 54 | 100.000 mM NaAc/acetic acid pH: 4.5 | 25.000% w/v PEG-3350 2100.000 mM Sodium formate | 100.000 mM CaCl2 |
| 55 | 100.000 mM NaAc/acetic acid pH: 4.5 | 750.000 mM (NH4)2 sulfate 5.000% v/v isopropanol 7.500% w/v PEG-3350 | |

TABLE 2-continued

| Well/Reagent | Compound Buffer | Precipitant | Additive |
|---|---|---|---|
| 56 | 1000.000 mM (NH4)3 citrate/citric acid pH: 5.5 | 1.000% w/v PEG-4000 | |
| 57 | 100.000 mM NaAc/acetic acid pH: 5.5 | 1.500% v/v MPD 12.000% w/v PEG 1500 2500.000 mM NaCl | |
| 58 | 100.000 mM imidazole/HCl pH: 6.5 | 2000.000 mM NaCl 20.000% w/v PEG-3350 | 100.000 mM MgCl2 |
| 59 | 100.000 mM imidazole/HCl pH: 6.5 | 4.000% w/v PEG-8000 3000.000 mM Sodium formate | |
| 60 | 1000.000 mM K2H phosphate/NaH2 phosphate pH: 7.5 | 0.500% w/v PEG-4000 | |
| 61 | 1400.000 mM K2H phosphate/NaH2 phosphate pH: 7.5 | 10.000% w/v PEG-3350 | |
| 62 | 800.000 mM (NH4)3 citrate/ammonium hydroxide pH: 8.5 | 2.000% w/v PEG-8000 | |
| 63 | 100.000 mM Tris base/HCl pH: 8.5 | 5.000% w/v PEG-4000 2000.000 mM NaCl | |
| 64 | 500.000 mM (NH4)3 citrate/ammonium hydroxide pH: 8.5 | 15.000% w/v PEG-8000 | |

TABLE 3

| Well/Reagent | Compound Buffer | Precipitant | Additive |
|---|---|---|---|
| 1 | 100.000 mM NaAc/acetic acid pH: 5.5 | 2000.000 mM (NH4)2 sulfate 2.000% v/v PEG-400 | |
| 2 | 100.000 mM imidazole/HCl pH: 6.5 | 2000.000 mM (NH4)2 sulfate 10.000% v/v glycerol | 100.000 mM magnesium sulfate |
| 3 | 100.000 mM HEPES/NaOH pH: 7.5 | 1.000% v/v MPD 2000.000 mM (NH4)2 sulfate | |
| 4 | 100.000 mM Tris base/HCl pH: 8.5 | 2000.000 mM (NH4)2 sulfate 5.000% v/v PEG-400 | 100.000 mM magnesium sulfate |
| 5 | 100.000 mM NaAc/acetic acid pH: 5.5 | 3900.000 mM NaCl 2.000% v/v PEG-400 | 100.000 mM MgCl2 |
| 6 | 100.000 mM imidazole/HCl pH: 6.5 | 5.000% v/v MPD 3000.000 mM NaCl | 100.000 mM CaCl2 |
| 7 | 100.000 mM HEPES/NaOH pH: 7.5 | 4000.000 mM NaCl 5.000% v/v isopropanol | |
| 8 | 2500.000 mM K2H phosphate/NaH2 phosphate pH: 5.5 | 5.000% v/v isopropanol | |
| 9 | 2000.000 mM K2H phosphate/NaH2 phosphate pH: 6.5 | 2.000% v/v PEG-400 | |
| 10 | 2500.000 mM K2H phosphate/NaH2 phosphate pH: 7.5 | 20.000% v/v glycerol | |
| 11 | 1000.000 mM K2H phosphate/NaH2 phosphate pH: 8.5 | 8.000% v/v MPD | |
| 12 | 2000.000 mM (NH4)3 citrate/citric acid pH: 4.5 | 1.000% v/v MPD | |
| 13 | 2000.000 mM (NH4)3 citrate/citric acid pH: 6.5. | 5.000% v/v isopropanol | |

TABLE 3-continued

| Well/Reagent | Compound Buffer | Precipitant | Additive |
|---|---|---|---|
| 14 | 2000.000 mM (NH4)3 citrate/citric acid pH: 7.5 | 5.000% v/v PEG-400 | |
| 15 | 100.000 mM NaAc/acetic acid pH: 4.5 | 5.000% v/v isopropanol 2000.000 mM Li2 sulfate | 100.000 mM magnesium sulfate |
| 16 | 100.000 mM NaAc/acetic acid pH: 5.5 | 2000.000 mM Li2 sulfate 5.000% v/v PEG-400 | 100.000 mM magnesium sulfate |
| 17 | 100.000 mM imidazole/HCl pH: 6.5 | 2000.000 mM Li2 sulfate 8.000% v/v MPD | |
| 18 | 100.000 mM Tris base/HCl pH: 8.5 | 2000.000 mM Li2 sulfate 2.000% v/v PEG-400 | |
| 19 | 100.000 mM NaAc/acetic acid pH: 4.5 | 15.000% v/v MPD 1000.000 mM Li2 sulfate | 100.000 mM magnesium sulfate |
| 20 | 750.000 mM (NH4)3 citrate/citric acid pH: 5.5 | 25.000% v/v MPD | |
| 21 | 100.000 mM imidazole/HCl pH: 6.5 | 1500.000 mM (NH4)2 sulfate 12.000% v/v isopropanol | |
| 22 | 100.000 mM imidazole/HCl pH: 6.5 | 30.000% v/v isopropanol 1300.000 mM NaCl | 100.000 mM CaCl2 |
| 23 | 100.000 mM HEPES/NaOH pH: 7.5 | 4000.000 mM NaCl 10.000% v/v PEG-400 | |
| 24 | 800.000 mM K2H phosphate/NaH2 phosphate pH: 7.5 | 20.000% v/v PEG-400 | |
| 25 | 1000.000 mM (NH4)3 citrate/ammonium hydroxide pH: 8.5 | 15.000% v/v isopropanol | |
| 26 | 100.000 mM Tris base/HCl pH: 8.5 | 15.000% v/v isopropanol 2.500% w/v PEG-3350 2000.000 mM Sodium formate | |
| 27 | 100.000 mM NaAc/acetic acid pH: 4.5 | 30.000% v/v MPD 25.000% w/v PEG 1500 | |
| 28 | 100.000 mM NaAc/acetic acid pH: 5.5 | 30.000% v/v MPD 15.000% w/v PEG-8000 | 100.000 mM CaCl2 |
| 29 | 100.000 mM imidazole/HCl pH: 6.5 | 30.000% v/v MPD 10.000% w/v PEG-3350 | 200.000 mM (NH4)2 sulfate |
| 30 | 100.000 mM HEPES/NaOH pH: 7.5 | 30.000% v/v MPD 4.000% w/v PEG 1500 | |
| 31 | 100.000 mM Tris base/HCl pH: 8.5 | 30.000% v/v MPD 8.000% w/v PEG-8000 | 500.000 mM NaCl |
| 32 | 100.000 mM NaAc/acetic acid pH: 5.5 | 30.000% v/v isopropanol 4.000% w/v PEG-3350 | 100.000 mM CaCl2 |

TABLE 3-continued

| Well/Reagent | Compound Buffer | Precipitant | Additive |
|---|---|---|---|
| 33 | 100.000 mM NaAc/acetic acid pH: 5.5 | 10.000% w/v PEG 1500 30.000% v/v isopropanol | 200.000 mM Li2 sulfate |
| 34 | 100.000 mM imidazole/HCl pH: 6.5 | 15.000% w/v PEG-8000 40.000% v/v isopropanol | |
| 35 | 200.000 mM (NH4)3 citrate/citric acid pH: 7.5 | 20.000% v/v isopropanol 15.000% w/v PEG-3350 | |
| 36 | 100.000 mM Tris base/HCl pH: 8.5 | 30.000% v/v isopropanol 30.000% w/v PEG-3350 | |
| 37 | 100.000 mM NaAc/acetic acid pH: 4.5 | 20.000% w/v PEG-8000 40.000% v/v PEG-400 | |
| 38 | 100.000 mM NaAc/acetic acid pH: 5.5 | 40.000% v/v PEG-400 5.000% w/v PEG-3350 | |
| 39 | 150.000 mM K2H phosphate/NaH2 phosphate pH: 6.5 | 15.000% w/v PEG 1000 40.000% v/v PEG-400 | |
| 40 | 100.000 mM HEPES/NaOH pH: 7.5 | 8.000% w/v PEG-8000 40.000% v/v PEG-400 | |
| 41 | 100.000 mM Tris base/HCl pH: 8.5 | 25.000% v/v PEG-400 20.000% w/v PEG-3350 | 100.000 mM MgCl2 |
| 42 | 100.000 mM NaAc/acetic acid pH: 5.5 | 3.000% v/v MPD 30.000% w/v PEG 1500 | 200.000 mM magnesium sulfate |
| 43 | 100.000 mM imidazole/HCl pH: 6.5 | 30.000% w/v PEG 1500 10.000% v/v isopropanol | 100.000 mM CaCl2 |
| 44 | 100.000 mM HEPES/NaOH pH: 7.5 | 30.000% w/v PEG 1500 20.000% v/v PEG-400 | |
| 45 | 100.000 mM Tris base/HCl pH: 8.5 | 8.000% v/v MPD 30.000% w/v PEG 1500 | |
| 46 | 200.000 mM (NH4)3 citrate/citric acid pH: 4.5 | 15.000% v/v isopropanol 25.000% w/v PEG-3350 | |
| 47 | 100.000 mM NaAc/acetic acid pH: 5.5 | 5.000% v/v PEG-400 25.000% w/v PEG-3350 | |
| 48 | 100.000 mM imidazole/HCl pH: 6.5 | 15.000% v/v MPD 25.000% w/v PEG-3350 | 200.000 mM Li2 sulfate |
| 49 | 100.000 mM HEPES/NaOH pH: 7.5 | 25.000% w/v PEG-3350 4.000% v/v isopropanol | 100.000 mM CaCl2 |
| 50 | 100.000 mM NaAc/acetic acid pH: 5.5 | 20.000% w/v PEG-8000 10.000% v/v PEG-400 | 500.000 mM NaCl |
| 51 | 100.000 mM imidazole/HCl pH: 6.5 | 3.000% v/v MPD 20.000% w/v PEG-8000 | |

TABLE 3-continued

| Well/Reagent | Compound Buffer | Precipitant | Additive |
|---|---|---|---|
| 52 | 100.000 mM HEPES/NaOH pH: 7.5 | 20.000% w/v PEG-8000 10.000% v/v isopropanol | 200.000 mM (NH4)2 sulfate |
| 53 | 100.000 mM Tris base/HCl pH: 8.5 | 20.000% w/v PEG-8000 20.000% v/v PEG-400 | 100.000 mM MgCl2 |
| 54 | 100.000 mM NaAc/acetic acid pH: 4.5 | 25.000% w/v PEG-3350 2100.000 mM Sodium formate | 100.000 mM CaCl2 |
| 55 | 100.000 mM NaAc/acetic acid pH: 4.5 | 750.000 mM (NH4)2 sulfate 5.000% v/v isopropanol 7.500% w/v PEG-3350 | |
| 56 | 1000.000 mM (NH4)3 citrate/citric acid pH: 5.5 | 1.000% w/v PEG-4000 | |
| 57 | 100.000 mM NaAc/acetic acid pH: 5.5 | 1.500% v/v MPD 12.000% w/v PEG 1500 2500.000 mM NaCl | |
| 58 | 100.000 mM imidazole/HCl pH: 6.5 | 2000.000 mM NaCl 20.000% w/v PEC-3350 | 100.000 mM MgCl2 |
| 59 | 100.000 mM imidazole/HCl pH: 6.5 | 4.000% w/v PEG-8000 3000.000 mM Sodium formate | |
| 60 | 1000.000 mM K2H phosphate/NaH2 phosphate pH: 7.5 | 0.500% w/v PEG-4000 | |
| 61 | 1400.000 mM K2H phosphate/NaH2 phosphate pH: 7.5 | 10.000% w/v PEG-3350 | |
| 62 | 800.000 mM (NH4)3 citrate/ammonium hydroxide pH: 8.5 | 2.000% w/v PEG-8000 | |
| 63 | 100.000 mM Tris base/HCl pH: 8.5 | 5.000% w/v PEG-4000 2000.000 mM NaCl | |
| 64 | 500.000 mM (NH4)3 citrate/ammonium hydroxide pH: 8.5 | 15.000% w/v PEG-8000 | |
| 65 | 100.000 mM NaAc/acetic acid pH: 5.5 | 1340.000 mM (NH4)2 sulfate 1.340% v/v PEG-400 | |
| 66 | 100.000 mM imidazole/HCl pH: 6.5 | 1340.000 mM (NH4)2 sulfate 6.700% v/v glycerol | 100.000 mM magnesium sulfate |
| 67 | 100.000 mM HEPES/NaOH pH: 7.5 | .67000% v/v MPD 1340.00 mM (NH4)2 sulfate | |
| 68 | 100.000 mM Tris base/HCl pH: 8.5 | 1340.000 mM (NH4)2 sulfate 3.350% v/v PEG-400 | 100.000 mM magnesium sulfate |
| 69 | 100.000 mM NaAc/acetic acid pH: 5.5 | 2613.000 mM NaCl 1.340% v/v PEG-400 | 100.000 mM MgCl2 |
| 70 | 100.000 mM imidazole/HCl pH: 6.5 | 3.350% v/v MPD 2010.00 mM NaCl | 100.000 mM CaCl2 |

TABLE 3-continued

| Well/Reagent | Compound Buffer | Precipitant | Additive |
|---|---|---|---|
| 71 | 100.000 mM HEPES/NaOH pH: 7.5 | 2680.000 mM NaCl<br>3.350% v/v isopropanol | |
| 72 | 1675.000 mM K2H phosphate/NaH2 phosphate pH: 5.5 | 3.350% v/v isopropanol | |
| 73 | 1340.000 mM K2H phosphate/NaH2 phosphate pH: 6.5 | 1.340% v/v PEG-400 | |
| 74 | 1675.000 mM K2H phosphate/NaH2 phosphate PH: 7.5 | 13.400% v/v glycerol | |
| 75 | 670.000 mM K2H phosphate/NaH2 phosphate pH: 8.5 | 5.360% v/v MPD | |
| 76 | 1340.000 mM (NH4)3 citrate/citric acid pH: 4.5 | .6700% v/v MPD | |
| 77 | 1340.000 mM (NH4)3 citrate/citric acid pH: 7. | 3.350% v/v isopropanol | |
| 78 | 1340.000 mM (NH4)3 citrate/citric acid pH: 7. | 3.350% v/v PEG-400 | |
| 79 | 100.000 mM NaAc/acetic acid pH: 4.5 | 3.350% v/v isopropanol<br>1340.00 mM Li2 sulfate | 100.000 mM magnesium sulfate |
| 80 | 100.000 mM NaAc/acetic acid pH: 5.5 | 1340.00 mM Li2 sulfate<br>3.350% v/v PEG-400 | 100.000 mM magnesium sulfate |
| 81 | 100.000 mM imidazole/HCl pH: 6.5 | 1340.000 mM Li2 sulfate<br>5.360% v/v MPD | |
| 82 | 100.000 mM Tris base/HCl pH: 8.5 | 1340.00 mM Li2 sulfate<br>1.340% v/v PEG-400 | |
| 83 | 100.000 mM NaAc/acetic acid pH: 4.5 | 10.050% v/v MPD<br>670.00 mM Li2 sulfate | 100.000 mM magnesium sulfate |
| 84 | 502.500 mM (NH4)3 citrate/citric acid pH: 5.5 | 16.750% v/v MPD | |
| 85 | 100.000 mM imidazole/HCl pH: 6.5 | 1005.00 mM (NH4)2 sulfate<br>8.040% v/v isopropanol | |
| 86 | 100.000 mM imidazole/HCl pH: 6.5 | 20.100% v/v isopropanol<br>871.00 mM NaCl | 100.000 mM CaCl2 |
| 87 | 100.000 mM HEPES/NaOH pH: 7.5 | 2680.000 mM NaCl<br>6.700% v/v PEG-400 | |
| 88 | 536.000 mM K2H phosphate/NaH2 phosphate pH: 7.5 | 13.400% v/v PEG-400 | |
| 89 | 670.000 mM (NH4)3 citrate/ammonium hydroxide pH: 8.5 | 10.050% v/v isopropanol | |
| 90 | 100.000 mM Tris base/HCl pH: 8.5 | 10.050% v/v isopropanol<br>1.6750% w/v PEG-3350<br>1340.00 mM Sodium formate | |
| 91 | 100.000 mM NaAc/acetic acid pH: 4.5 | 20.100% v/v MPD<br>16.750% w/v PEG 1500 | |

TABLE 3-continued

| Well/Reagent | Compound Buffer | Precipitant | Additive |
|---|---|---|---|
| 92 | 100.000 mM NaAc/acetic acid pH: 5.5 | 20.100% v/v MPD 10.050% w/v PEG-8000 | 100.000 mM CaCl2 |
| 93 | 100.000 mM imidazole/HCl pH: 6.5 | 20.100% v/v MPD 6.700% w/v PEG-3350 | 200.000 mM (NH4)2 sulfate |
| 94 | 100.000 mM HEPES/NaOH pH: 7.5 | 20.100% v/v MPD 2.680% w/v PEG 1500 | |
| 95 | 100.000 mM Tris base/HCl pH: 8.5 | 20.100% v/v MPD 5.360% w/v PEG-8000 | 500.000 mM NaCl |
| 96 | 100.000 mM NaAc/acetic acid pH: 4.5 | 20.100% v/v isopropanol 2.680% w/v PEG-3350 | 100.000 mM CaCl2 |
| 97 | 100.000 mM NaAc/acetic acid pH: 5.5 | 6.700% w/v PEG 1500 20.100% v/v isopropanol | 200.000 mM Li2 sulfate |
| 98 | 100.000 mM imidazole/HCl pH: 6.5 | 10.0500% w/v PEG-8000 26.800% v/v isopropanol | |
| 99 | 200.000 mM (NH4)3 citrate/citric acid pH: 7.5 | 13.400% v/v isopropanol 10.050% w/v PEG-3350 | |
| 100 | 100.000 mM Tris base/HCl pH: 8.5 | 20.100% v/v isopropanol 20.100% w/v PEG-3350 | |
| 101 | 100.000 mM NaAc/acetic acid pH: 4.5 | 13.400% w/v PEG-8000 26.800% v/v PEG-400 | |
| 102 | 100.000 mM NaAc/acetic acid pH: 5.5 | 26.800% v/v PEG-400 3.350% w/v PEG-3350 | |
| 103 | 150.000 mM K2H phosphate/NaH2 phosphate pH: 6.5 | 10.050% w/v PEG 1000 26.800% v/v PEG-400 | |
| 104 | 100.000 mM HEPES/NaOH pH: 7.5 | 5.360% w/v PEG-8000 26.800% v/v PEG-400 | |
| 105 | 100.000 mM Tris base/HCl pH: 8.5 | 16.750% v/v PEG-400 13.400% w/v PEG-3350 | 100.000 mM MgCl2 |
| 106 | 100.000 mM NaAc/acetic acid pH: 5.5 | 2.010% v/v MPD 20.100% w/v PEG 1500 | 200.000 mM magnesium sulfate |
| 107 | 100.000 mM imidazole/HCl pH: 6.5 | 20.100% v/v PEG 1500 6.700% v/v isopropanol | 100.000 mM CaCl2 |
| 108 | 100.000 mM HEPES/NaOH pH: 7.5 | 20.100% v/v PEG 1500 13.400% v/v PEG-400 | |
| 109 | 100.000 mM Tris base/HCl pH: 85 | 5.360% v/v MPD 20.100% w/v PEG 1500 | |
| 110 | 200.000 mM (NH4)3 citrate/citric acid pH: 4.5 | 10.050% v/v isopropanol 16.750% w/v PEG-3350 | |

TABLE 3-continued

| Well/Reagent | Compound Buffer | Precipitant | Additive |
|---|---|---|---|
| 111 | 100.000 mM NaAc/acetic acid pH: 5.5 | 3.350% v/v PEG-400 16.750% w/v PEG-3350 | |
| 112 | 100.000 mM imidazole/HCl pH: 6.5 | 10.050% v/v MPD 16.750% w/v PEG-3350 | 200.000 mM Li2 sulfate |
| 113 | 100.000 mM HEPES/NaOH pH: 7.5 | 16.750% w/v PEG-3350 2.680% v/v isopropanol | 100.000 mM CaCl2 |
| 114 | 100.000 mM NaAc/acetic acid pH: 5.5 | 13.400% w/v PEG-8000 6.700% v/v PEG-400 | 500.000 mM NaCl |
| 115 | 100.000 mM imidazole/HCl pH: 6.5 | 2.010% v/v MPD 13.400% w/v PEG-8000 | |
| 116 | 100.000 mM HEPES/NaOH pH: 7.5 | 13.400% w/v PEG-8000 6.700% v/v isopropanol | 200.000 mM (NH4)2 sulfate |
| 117 | 100.000 mM Tris base/HCl pH: 8.5 | 13.400% w/v PEG-8000 13.400% v/v PEG-400 | 100.000 mM MgCl2 |
| 118 | 100.000 mM NaAc/acetic acid pH: 4.5 | 16.750% w/v PEG-3350 1407.00 mM Sodium formate | 100.000 mM CaCl2 |
| 119 | 100.000 mM NaAc/acetic acid pH: 4.5 | 502.50 mM (NH4)2 sulfate 3.350% v/v isopropanol 7.500% w/v PEG-3350 | |
| 120 | 670.000 mM (NH4)3 citrate/citric acid pH: 5.5 | .6700% w/v PEG-4000 | |
| 121 | 100.000 mM NaAc/acetic acid pH: 5.5 | 1.005% v/v MPD 8.040% w/v PEG 1500 1675.00 mM NaCl | |
| 122 | 100.000 mM imidazole/HCl pH: 6.5 | 13.400% w/v PEG-3350 1340.000 mM NaCl | 100.000 mM MgCl2 |
| 123 | 100.000 mM imidazole/HCl pH: 6.5 | 2.680% w/v PEG-8000 2010.00 mM Sodium formate | |
| 124 | 670.000 mM K2H phosphate/NaH2 phosphate pH: 7.5 | .3350% w/v PEG-4000 | |
| 125 | 938.000 mM K2H phosphate/NaH2 phosphate pH: 7.5 | 6.700% w/v PEG-3350 | |
| 126 | 536.000 mM (NH4)3 citrate/ammonium hydroxide pH: 8.5 | 1.340% w/v PEG-8000 | |
| 127 | 100.000 mM Tris base/HCl pH: 8.5 | 3.350% w/v PEG-4000 1340.00 mM NaCl | |
| 128 | 335.000 mM (NH4)3 citrate/ammonium hydroxide pH: 8.5 | 10.050% w/v PEG-8000 | |
| 129 | 100.000 mM NaAc/acetic acid pH: 5.5 | 660.00 mM (NH4)2 sulfate .660% v/v PEG-400 | |

TABLE 3-continued

| Well/Reagent | Compound Buffer | Precipitant | Additive |
|---|---|---|---|
| 130 | 100.000 mM imidazole/HCl pH: 6.5 | 660.000 mM (NH4)2 sulfate 3.300% v/v glycerol | 100.000 mM magnesium sulfate |
| 131 | 100.000 mM HEPES/NaOH pH: 7.5 | .330% v/v MPD 660.00 mM (NH4)2 sulfate | |
| 132 | 100.000 mM Tris base/HCl pH: 8.5 | 660.00 mM (NH4)2 sulfate 1.650% v/v PEG-400 | 100.000 mM magnesium sulfate |
| 133 | 100.000 mM NaAC/acetic acid pH: 5.5 | 1287.000 mM NaCl .660% v/v PEG-400 | 100.000 mM MgCl2 |
| 134 | 100.000 mM imidazole/HCl pH: 6.5 | 1.650% v/v MPD 990.000 mM NaCl | 100.000 mM CaCl2 |
| 135 | 100.000 mM HEPES/NaOH pH: 7.5 | 1.650% v/v isopropanol 1320.000 mM NaCl | |
| 136 | 825.000 mM K2H phosphate/NaH2 phosphate pH: 5.5 | 1.650% v/v isopropanol | |
| 137 | 660.000 mM K2H phosphate/NaH2 phosphate pH: 6.5 | .660% v/v PEG-400 | |
| 138 | 825.000 mM K2H phosphate/NaH2 phosphate pH: 7.5 | 6.600% v/v glycerol | |
| 139 | 330.000 mM K2H phosphate/NaH2 phosphate pH: 8.5 | 2.640% v/v MPD | |
| 140 | 660.000 mM (NH4)3 citrate/citric acid pH: 4.5 | .330% v/v MPD | |
| 141 | 660.000 mM (NH4)3 citrate/citric acid pH: 7. | 1.650% v/v isopropanol | |
| 142 | 660.000 mM (NH4)3 citrate/citric acid pH: 7. | 1.650% v/v PEG-400 | |
| 143 | 100.000 mM NaAc/acetic acid pH: 4.5 | 1.650% v/v isopropanol 660.000 mM Li2 sulfate | 100.000 mM magnesium sulfate |
| 144 | 100.000 mM NaAc/acetic acid pH: 5.5 | 660.000 mM Li2 sulfate 1.650% v/v PEG-400 | 100.000 mM magnesium sulfate |
| 145 | 100.000 mM imidazole/HCl pH: 6.5 | 660.000 mM Li2 sulfate 2.640% v/v MPD | |
| 146 | 100.000 mM Tris base/HCl pH: 8.5 | 660.000 mM Li2 sulfate .660% v/v PEG-400 | |
| 147 | 100.000 mM NaAc/acetic acid pH: 4.5 | 4.950% v/v MPD 330.000 mM Li2 sulfate | 100.000 mM magnesium sulfate |
| 148 | 247.500 mM (NH4)3 citrate/citric acid pH: 5.5 | 8.250% v/v MPD | |
| 149 | 100.000 mM imidazole/HCl pH: 6.5 | 495.000 mM (NH4)2 sulfate 3.960% v/v isopropanol | |
| 150 | 100.000 mM imidazole/HCl pH: 6.5 | 9.900% v/v isopropanol 429.000 mM NaCl | 100.000 mM CaCl2 |
| 151 | 100.000 mM HEPES/NaOH pH: 7.5 | 1320.000 mM NaCl 3.300% v/v PEG-400 | |

TABLE 3-continued

| Well/Reagent | Compound Buffer | Precipitant | Additive |
|---|---|---|---|
| 152 | 264.000 mM K2H phosphate/NaH2 phosphate pH: 7.5 | 6.600% v/v PEG-400 | |
| 153 | 330.000 mM (NH4)3 citrate/ammonium hydroxide pH: 8.5 | 4.950% v/v isopropanol | |
| 154 | 100.000 mM Tris base/HCl pH: 8.5 | 4.950% v/v isopropanol 0.825% w/v PEG-3350 660.000 mM Sodium formate | |
| 155 | 100.000 mM NaAc/acetic acid pH: 4.5 | 9.900% v/v MPD 8.250% w/v PEG 1500 | |
| 156 | 100.000 mM NaAc/acetic acid pH: 5.5 | 9.900% v/v MPD 4.950% w/v PEG-8000 | 100.000 mM CaCl2 |
| 157 | 100.000 mM imidazole/HCl pH: 6.5 | 9.900% v/v MPD 3.300% w/v PEG-3350 | 200.000 mM (NH4)2 sulfate |
| 158 | 100.000 mM HEPES/NaOH pH: 7.5 | 9.900% v/v MPD 1.320% w/v PEG 1500 | |
| 159 | 100.000 mM Tris base/HCl pH: 8.5 | 9.900% v/v MPD 2.640% w/v PEG-8000 | 500.000 mM NaCl |
| 160 | 100.000 mM NaAc/acetic acid pH: 4.5 | 9.900% v/v isopropanol 1.320% w/v PEG-3350 | 100.000 mM CaCl2 |
| 161 | 100.000 mM NaAc/acetic acid pH: 5.5 | 3.300% w/v PEG 1500 9.900% v/v isopropanol | 200.000 mM Li2 sulfate |
| 162 | 100.000 mM imidazole/HCl pH: 6.5 | 4.950% w/v PEG-8000 13.20% v/v isopropanol | |
| 163 | 200.000 mM (NH4)3 citrate/citric acid pH: 7.5 | 6.600% v/v isopropanol 4.950% w/v PEG-3350 | |
| 164 | 100.000 mM Tris base/HCl pH: 8.5 | 9.900% v/v isopropanol 9.900% w/v PEG-3350 | |
| 165 | 100.000 mM NaAc/acetic acid pH: 4.5 | 6.600% w/v PEG-8000 13.200% v/v PEG-400 | |
| 166 | 100.000 mM NaAc/acetic acid pH: 5.5 | 13.200% v/v PEG-400 1.650% w/v PEG-3350 | |
| 167 | 150.000 mM K2H phosphate/NaH2 phosphate pH: 6.5 | 4.950% w/v PEG 1000 13.20% v/v PEG-400 | |
| 168 | 100.000 mM HEPES/NaOH pH: 7.5 | 2.640% w/v PEG-8000 13.20% v/v PEG-400 | |
| 169 | 100.000 mM Tris base/HCl pH: 8.5 | 8.250% v/v PEG-400 6.600% w/v PEG-3350 | 100.000 mM MgCl2 |
| 170 | 100.000 mM NaAc/acetic acid pH: 5.5 | .990% v/v MPD 9.900% w/v PEG 1500 | 200.000 mM magnesium sulfate |
| 171 | 100.000 mM imidazole/HCl pH: 6.5 | 9.900% w/v PEG 1500 3.300% v/v isopropanol | 100.000 mM CaCl2 |

TABLE 3-continued

| Well/Reagent | Compound Buffer | Precipitant | Additive |
|---|---|---|---|
| 172 | 100.000 mM HEPES/NaOH pH: 7.5 | 9.900% w/v PEG 1500<br>6.600% v/v PEG-400 | |
| 173 | 100.000 mM Tris base/HCl pH: 8.5 | 2.640% v/v MPD<br>9.900% w/v PEG 1500 | |
| 174 | 200.000 mM (NH4)3 citrate/citric acid pH: 4.5 | 4.950% v/v isopropanol<br>8.250% w/v PEG-3350 | |
| 175 | 100.000 mM NaAc/acetic acid pH: 5.5 | 1.650% v/v PEG-400<br>8.250% w/v PEG-3350 | |
| 176 | 100.000 mM imidazole/HCl pH: 6.5 | 4.950% v/v MPD<br>8.250% w/v PEG-3350 | 200.000 mM Li2 sulfate |
| 177 | 100.000 mM HEPES/NaOH pH: 7.5 | 8.250% w/v PEG-3350<br>1.320% v/v isopropanol | 100.000 mM CaCl2 |
| 178 | 100.000 mM NaAc/acetic acid pH: 5.5 | 6.600% w/v PEG-8000<br>3.300% v/v PEG-400 | 500.000 mM NaCl |
| 179 | 100.000 mM imidazole/HCl pH: 6.5 | .990% v/v MPD<br>6.60% w/v PEG-8000 | |
| 180 | 100.000 mM HEPES/NaOH pH: 7.5 | 6.600% w/v PEG-8000<br>3.300% v/v isopropanol | 200 mM (NH4)2 sulfate |
| 181 | 100.000 mM Tris base/HCl pH: 8.5 | 6.600% w/v PEG-8000<br>6.600% v/v PEG-400 | 100.000 mM MgCl2 |
| 182 | 100.000 mM NaAc/acetic acid pH: 4.5 | 8.250% w/v PEG-3350<br>693.000 mM Sodium formate | 100.000 mM CaCl2 |
| 183 | 100.000 mM NaAc/acetic acid pH: 4.5 | 247.500 mM (NH4)2 sulfate<br>1.650% v/v isopropanol<br>2.475% w/v PEG-3350 | |
| 184 | 330.000 mM (NH4)3 citrate/citric acid pH: 5.5 | 0.330% w/v PEG-4000 | |
| 185 | 100.000 mM NaAc/acetic acid pH: 5.5 | .495% v/v MPD<br>3.960% w/v PEG 1500<br>825.000 mM NaCl | |
| 186 | 100.000 mM imidazole/HCl pH: 6.5 | 660.000 mM NaCl<br>6.600% w/v PEG-3350 | 100.000 mM MgCl2 |
| 187 | 100.000 mM imidazole/HCl pH: 6.5 | 1.320% w/v PEG-8000<br>990.000 mM Sodium formate | |
| 188 | 330.000 mM K2H phosphate/NaH2 phosphate pH: 7.5 | 0.165% w/v PEG-4000 | |
| 189 | 462.000 mM K2H phosphate/NaH2 phosphate pH: 7.5 | 3.300% w/v PEG-3350 | |
| 190 | 264.000 mM (NH4)3 citrate/ammonium hydroxide pH: 8.5 | 0.660% w/v PEG-8000 | |
| 191 | 100.000 mM Tris base/HCl pH: 8.5 | 1.650% w/v PEG-4000<br>2000.000 mM NaCl | |

TABLE 3-continued

| Well/Reagent | Compound Buffer | Precipitant | Additive |
|---|---|---|---|
| 192 | 165.000 mM (NH4)3 citrate/ammonium hydroxide pH: 8.5 | 4.950% w/v PEG-8000 | |

TABLE 4

Comparison of standard and PS crystallization screens.

| Protein orComplex | Hampton Crystallization Screen (Standard) | | | | Precipitation Synergy Screen (PS) | | | | Hampton + PS Screen | | |
|---|---|---|---|---|---|---|---|---|---|---|---|
| | Hampton condition with crystals† | Number of conditions | Different space groups | Suitable for structural analysis | PS condition with crystals† | Number of conditions | Different space groups | Suitable for structural analysis | Initial | Different space groups | Suitable for structural analysis |
| scFv 17b/D1D2/gp120: HXBc2Δ82ΔV1, 2ΔV3ΔC5¶ | 9, 41 | 2* | 0 | 0 | 43, 45 | 2 | 0 | 0 | 4 | 0 | 0 |
| Fab 17b/D1D2/gp120: HXBc2ΔV1, 2ΔV3 | 5, 14, 32 | 3 | 0 | 0 | 29, 43, 49 | 3 | 0 | 0 | 6 | 0 | 0 |
| Fab 17b/D1D2/gp120: YU2 Δ82ΔV1, 2ΔV3ΔC5 | 14, 18, 28, 40, 43 | 5* | 3* | 1*¥ | 39, 48 | 2 | 1 | 0 | 7 | 3 | 1 |
| Fab 48d/D1D2/gp120: HXBc2ΔV1,2ΔV3 | 17, 18, 38, 40, 46 | 5* | 2* | 0 | 9, 46 | 2 | 2 | 0 | 7 | 2 | 0 |
| Fab 48d/D1D2/gp120: YU2ΔV1, 2ΔV3 | 5, 8, 14, 19 | 4 | 0 | 0 | — | 0 | 0 | 0 | 4 | 0 | 0 |
| Fab 48d/Fab 211c/D1D2/gp120: YU2ΔV1, 2ΔV3 | 5, 8 | 2 | 0 | 0 | — | 0 | 0 | 0 | 2 | 0 | 0 |
| Fab 412d/D1D2/gp120: YU2 Δ82ΔV1, 2ΔV3ΔC5 | — | 0 | 0 | 0 | 17 | 1 | 0 | 0 | 1 | 0 | 0 |
| Fab 17b | — | 0 | 0 | 0 | 11, 17 | 2 | 1 | 1 | 2 | 1 | 1 |
| Fab 47c | — | 0 | 0 | 0 | 36, 56 | 2 | 1 | 1 | 2 | 1 | 1 |
| Fab 48d | 9, 12, 40 | 3* | 1* | 1* | 11, 13, 14, 30, 60 | 5 | 1 | 1 | 8 | 1 | 1 |
| 4-domain CD4# | — | 0 | 0 | 0 | 4 | 1 | 6 | 3 | 1 | 6 | 3 |
| Σ | | 24 | 6 | 2 | | 20 | 12 | 6 | 44 | 14 | 7 |

†Adjustment of precipitant concentration often required for crystallization (see methods).
¶The gp120 construct is reported here by isolate (HXBc2 or YU2) and then by deletion, with core gp120 consisting of Δ82ΔV1, 2ΔV3ΔC5 (see [48]).
*These Hampton conditions involved precipitant mixtures.
¥The structure of this YU2 crystal was reported previously [25].
CD4 crystallization reported previously [16, 49].

TABLE 5

Optimized crystallization condition for HIV-envelope-related proteins

| Protein Or Complex† | Space Group | Diffraction Limit | Crystal Lattice* | | | | | | Crystallization Conditions | | | |
|---|---|---|---|---|---|---|---|---|---|---|---|---|
| | | | Cell Constants. | | | | | | Salt | (HMW) PEG | Organic | pH |
| | | | a | b | c | α | β | γ | | | | |
| Fab17b/D1D2/gp120 YU2 Δ82ΔV1, 2ΔV3ΔC5 | P1 | 3.5 | 83.60 | 75.44 | 98.83 | 90.0 | 115.1 | 90.0 | 0.06M MgAcetate | 6.4% PEG 8000 | 4.5% Isopropanol | 6.5 |
| Fab17b/D1D2/gp120 YU2 Δ82ΔV1, 2ΔV3ΔC5 | C2 | 2.8 | 174.99 | 81.71 | 74.48 | 90 | 90.4 | 90 | 0.07M MgAcetate + 0.3M NaCl | 7.0% PEG 8000 | 18.0% Ethanol | 6.5 |

TABLE 5-continued

Optimized crystallization condition for HIV-envelope-related proteins

| Protein Or Complex† | Crystal Lattice* | | | | | | | | Crystallization Conditions | | | |
|---|---|---|---|---|---|---|---|---|---|---|---|---|
| | Space Group | Diffraction Limit | Cell Constants | | | | | | Salt | (HMW) PEG | Organic | pH |
| | | | a | b | c | α | β | γ | | | | |
| Fab17b/ D1D2/gp120 YU2 Δ82ΔV1, 2ΔV3ΔC5 | C2 | 5.0 | 199.3 | 77.7 | 161.3 | 90 | 107.7 | 90 | 0.07M Li$_2$SO$_4$ | 9.1% PEG 3350 | 5.4% MPD | 6.5 |
| Fab48d/ D1D2/gp 120 HxBc2ΔV1, 2ΔV3 | P2$_1$ | 7.0 | 93.3 | 195.2 | 88.9 | 90 | 101.0 | 90 | 0.38M Li$_2$SO$_4$ | 6.8% PEG 4000 | 6.8% Isopropanol | 6.5 |
| Fab48d/ D1D2/gp 120 HxBc2ΔV1, 2ΔV3 | P2$_1$ | 7.0 | 90 | 200 | 90 | 90 | 100 | 90 | 1.3M Na/KPO$_4$ + 0.4M NaCl | — | 1.3% PEG 400 | 6.5 |
| Fab48d/ D1D2/gp 120 HxBc2ΔV1, 2ΔV3 | C222 | 10 | 197.1 | 342.3 | 140.2 | 90 | 90 | 90 | — | 8.3% PEG 4000 | 8.3% Isopropanol | 5.6 |
| Fab48d/ D1D2/gp 120 HxBc2ΔV1, 2ΔV3 | C222 | 10 | 200 | 340 | 140 | 90 | 90 | 90 | 1.9M Na/KPO$_4$ | — | 3.9% PEG 400 | 6.5 |
| Fab 17b | P2$_1$2$_1$2$_1$ | 2.2 | 63.21 | 117.46 | 154.81 | 90 | 90 | 90 | 2.0M Am$_2$SO$_4$ | — | 10% MPD | 7.5 |
| Fab 47e | P1 | 2.9 | 73.43 | 111.64 | 133.31 | 85.5 | 90.0 | 89.7 | 1.2M Am$_2$Citrate | 4.0% PEG 1000 | — | 9.0 |
| Fab, 48d¶ | P2$_1$2$_1$2$_1$ | 2.0 | 64.09 | 73.45 | 103.42 | 90 | 90 | 90 | 0.3M NaCl | 8.9% PEG 4000 | 8.9% Isopropanol | 5.6 |
| 4-domain CD4 | P2 | 4.0 | 105.0 | 123.4 | 100.6 | 90 | 103.4 | 90 | 0.2M Am$_2$SO$_4$ | — | 30% PEG 400 | 8.5 |
| 4-domain CD4 | P2 | 5.2 | 110 | 125 | 98 | 90 | 99.5 | 90 | 0.3M Am$_2$SO$_4$ | — | 30% PEG 400 | 8.7 |
| 4-domain CD4 | C2 | 5.9 | 227 | 168 | 141 | 90 | 119.8 | 90 | 2.0M Am$_2$SO$_4$ | — | 2.5% PEG 400 | 8.4 |
| 4-domain CD4 | P3$_1$21 | 5.0 | 126 | 126 | 205 | 90 | 90 | 120 | 2.5M Am$_2$PO$_4$ | — | 2.0% PEG 400 | 8.7 |
| 4-damain CD4 | P4$_3$22 | 3.9 | 127.1 | 127.1 | 221.2 | 90 | 90 | 90 | 0.3M Am$_2$SO$_4$ | — | 40% PEG 400 | 8.8 |
| 4-domain CD4 | P4$_1$22/ P4$_3$22 | 7.5 | 123 | 123 | 395 | 90 | 90 | 90 | 2.0M Am$_2$SO$_4$ | — | 2.5% PEG 400 | 8.4 |

†Crystals described in rows highlighted in bold were suitable for structural analysis and have been solved (refs [25, 49] and C. H. unpublished data)
¶Of the 18 crystals described in Table 4 for which space group parameters could be determined, optimization from Hampton and PS initial conditions converged on similar crystallization conditions for these 2 crystal forms.
*Diffraction limit and cell constants (a, b, c) are reported in Å, whereas angles (α, β, γ) are reported in degrees.

SUPPLEMENTAL EXAMPLE

Crystallization Screens

The most efficient means to identify crystallization conditions have incorporated sparse matrix or factorial screening technology [6, 7]. These screens sample combinations of independent factors that affect crystallization. Unfortunately, current screens treat the precipitating agent as a single variable, whereas high salt, high molecular weight PEGs and organic solvents function through completely different mechanisms. Thus treating the precipitant as a single variable is equivalent to using a screen that keeps the pH as a single variable, never mixing different pHs with different precipitants.

The instant method, i.e., crystallization reagent identification method or "screen", utilizes combinations of mechanistically different precipitating agents [50]. Tests with hen-egg white lysozyme produced an entirely new lattice, the first new lysozyme lattice to be identified since 1967 (this despite the proliferation of many new screens over the past 30 years). Tests with 10 proteins showed that this screen roughly tripled the number of different crystals compared to the Hampton Crystal screen. This screen thus not only increases the probability of obtaining crystals, it also screens conditions not found in any of the other commercial screens.

The subject screen is envisioned, for example, in two formats: a 64-reagent format and a 192-reagent format. The 64-reagent format sets the precipitants at a high level, close to the solubility point of the precipitants. In order to use this screen effectively, each condition needs to be tested and diluted so that the protein being screened is at the precipitation point. The 192-format has the 64 conditions at three precipitant concentrations, 100%, 67% and 33%. The 67% and 33% formulations maintain the buffer and additive concentrations at the 100% level, allowing effective buffering and additive variation even if the protein being tested requires low concentrations of precipitant. The 192-format is also the most suitable for robotic screening.

Each of the screen formats can be made available, for example, in different sizes (e.g., a 1 ml/reagent trial format and a 10 ml/reagent production format). In addition to initial crystal screening, the reagents used in this screen can also be used in optimization of suboptimal crystals [50]. Once an initial crystallization condition (reagent) has been identified, it can be mixed with 5-10% of each of the reagents used in the screen, allowing a localized precipitant synergy sparse matrix. Thus in the same manner that protein concentration, pH and other factors can be used in optimization, the reagents used in the subject method provide a means to immediately improve suboptimal crystals.

Screen Reagent Kits:

64-reagent format

Trial format (1 ml of each reagent)

Production format (10 ml of each reagent)

Optimization format (0.5 ml of each reagent)
192-reagent format
Trial format (1 ml of each reagent)
Production format (10 ml of each reagent)
Optimization format (0.5 ml of each reagent)

REFERENCES

1. Hendrickson, W. A. (2000). Synchrotron crystallography. Trends Biochem. Sci. 25, 637-643.
2. Shapiro, L. and Lima, C. D. (1998). The Argonne structural genomics workshop: Lamaze class for the birth of a new science. Structure 6, 265-267.
3. Stevens, R. C. and Wilson, I. A. (2001). Industrializing structural biology. Science 293, 519-520.
4. Ducruix, A. and Giege, R. (1992) Crystallization of nucleic acids and proteins, Oxford University Press, Oxford.
5. McPherson, A. (1999) Crystallization of Biological Macromolecules, 1st ed., Cold Spring Harbor Laboratory Press, Cold Spring Harbor, N.Y.
6. Carter, C. W. Jr. and Carter, C. W. (1979). Protein crystallization using incomplete factorial experiments. J. Biol. Chem. 254, 12219-12223.
7. Jancarik, J. and Kim, S. H. (1991). Sparse matrix sampling: a screening method for crystallization of proteins. J. Appl. Cryst. 24, 409-411.
8. Hofmeister, F. (1888). Zur Lehre von der Wirkung der Salze. Fiaunyn-Schmiedebergs Arch. Exp. Pathol. Pharmakol. 24, 247.
9. Askonas, B. A. (1951). The use of organic solvents at low temperature for the separation of enzymes: Application to aqueous rabbit muscle extract. Biochem. J. 48, 42-48.
10. Polson, A., Ptgieter, J. F., Largier, J. F., Mears, G. E. F. and Joubert, F. J. (1964). The fractionation of protein mixtures by linear polymers of high molecular weight. Biochim. Biophys. Acta 82, 463-475.
11. McPherson, A. (1976). Crystallization of proteins from polyethylene glycol. J. Biol. Chem. 251, 6300-6303.
12. Carter, C. W., Jr. (1999) in Crystallization of nucleic acids and proteins (Ducruix, A. and Giege, R., eds.), second ed., pp. 95, Oxford University Press, Oxford.
13. Collier, R. J., Westbrook, E. M., McKay, D. B. and Eisenberg, D. (1982). X-ray grade crystals of Diphtheria Toxin. J. Biol. Chem. 257, 5283-5285.
14. Collier, R. J. and McKay, D. B. (1982). Crystallization of exotoxin A from pseudomonas aeruginosa. J. Mol. Biol. 157, 413-415.
15. Kuciel, R., Jakob, C. G. and Lebioda, L. (1992). Crystallization of human prostatic acid phosphatase using biphasic systems. J. Cryst. Growth 122, 199-203.
16. Kwong, P. D., Ryu, S. -E., Hendrickson, W. A., Axel, R., Sweet, R. M., Folena-Wasserman, G., Hensley, P. and Sweet, R. W. (1990). Molecular characteristics of recombinant human CD4 as deduced from polymorphic crystals. Proc. Natl. Acad. Sci. USA 87, 6423-6427.
17. Qian, C. G., Lagace, L., Massariol, M. J., Chabot, C., Yoakim, C., Deziel, R. and L., T. (2000). A rational approach towards successful crystallization and crystal treatment of human cytomegalovirus protease and its inhibitor complex. Acta Crystallogr. D56, 175-180.
18. Ray, W. J. and Puvathingal, J. M. (1986). The effect of polyethylene glycol on the growth and dissolution rates of a crystalline protein at high salt concentration. Phosphoglucomutase. J. Biol. Chem. 276, 11544-11549.
19. Sousa, R. (1997). Using cosolvents to stabilize protein conformation for crystallization. Methods Enzymol 276, 131-143.
20. McPherson, A. (2001). A comparison of salts for the crystallization of macromolecules. Protein Science 10, 418-422.
21. Radaev, S. and Sun, P. D. (2002). Crystallization of protein-protein complexes. J. Appl. Crystallogr. 35, 674-676.
22. Patel, S., Cudney, B. and McPherson, A. (1995). Polymeric precipitants for the crystallization of macromolecules. Biochem. Bioph. Reg. Comm. 207, 819-828.
23. Kwong, P. D., Wyatt, R., Desjardins, E., Robinson, J., Culp, J. S., Helimig, B. D., Sweet, R. W., Sodroski, J. and Hendrickson, W. A. (1999). Probability analysis of variational crystallization and its application to gp120, the exterior envelope glycoprotein of type 1 human immunodeficiency virus (HIV-1). J. Biol. Chem. 274, 4115-4123.
24. Saphire, E. O., Parren, P. W., Pantophlet, R., Zwick, M. B., Morris, G. M., Rudd, P. M., Dwek, R. A., Stanfield, R. L., Burton, D. R. and Wilson, I. A. (2001). Crystal structure of a neutralizing human IgG against. HIV-1: a template for vaccine design. Science 293, 1155-1159.
25. Kwong, P. D., Wyatt, R., Majeed, S., Robinson, J., Sweet, R. W., Sodroski, J. and Hendrickson, W. A. (2000). Structures of HIV-1 gp120 envelope glycoproteins from laboratory-adapted and primary isolates. Structure 8, 1329-1339.
26. Palmer, K. J. (1947). Structure Reports 11, 729.
27. Crick, F. H. C. (1953). The unit cells of four proteins. Acta Cryst állogr. 6, 221-222.
28. Steinrauf, L. K. (1959). Preliminary X-ray data for some new crystalline forms of beta-lactoglobulin and hen egg-white lysozyme. Acta Crystallogr. 12, 77-79.
29. Haas, D. J. (1967). Preliminary X-ray data for two new forms of hen egg-white lysozyme. Acta Crystallogr. 23, 666.
30. Forsythe, E. L., Snell, E. H., Malone, C. C. and Pusey, M. L. (1999). Crystallization of chicken egg white lysozyme from assorted sulfate salts. J. Cryst. Growth 196, 332-343.
31. Wukovitz, S. W. and Yeates, T. O. (1995). Why protein crystals favour some space-groups over others. Nature Struct. Biol. 2, 1062-1067.
32. Audic, S., Lopez, F., Claverie, J. M., Poirot, O. and Abergel, C. (1997). SAmBA: An interactive software for optimizing the design of biological macromolecules crystallization experiments. Proteins: Structure, Function, Genetics 29, 252-257.
33. Timasheff, S. N. and Arakawa, T. (1988). Mechanism of protein precipitation and stabilization by co-solvents. J. Cryst. Growth 90, 39-46.
34. Shieh, H. S., Stallings, W. C., Steven, A. M. and Stegeman, R. A. (1995). Using sampling techniques in protein crystallization. J. Cryst. Growth 232, 553-562.
35. Segelke, B. W. (2001). Efficiency analysis of sampling protocols used in protein crystallization screening. J. Cryst. Growth 232, 553-562.
36. Song, L. and Gouaux, J. E. (1997). Membrane protein crystallization: application of sparse matrices to the alpha-Hemolysin heptamer. Methods Enzymol 276, 60-74.
37. Goodwill, K. E., Tennant, M. G. and Stevens, R. C. (2001). High-throughput X-ray crystallography for structure-based drug design. Drug Discovery Today 6, S113-S118.
38. Otwinowski, Z. and Minor, W. (1997). Processing of X-ray diffraction data collected in oscillation mode. Methods Enymol. 276, 307-326.
39. Navaza, J. (1994). AMoRe: an automated package for molecular replacement. Acta Crystallogr. A50, 157-163.
40. Sauter, C., Otalora, F., Gavira, J. A., Vidal, O., Giege, R. and Garcia-Ruiz, J. M. (2001). Structure of tetragonal hen egg-white lysozyme at 0.94 A from crystals grown by counter-diffusion method.
Acta Crystallogr. D57, 1119-1126.

41. Brunger, A. T. (1992) Yale University Press, New Haven, Conn.
42. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., et al. (1998). Crystallography & NMR system: A new software suite for macromolecular structure determination. Acta Crystallogr. D54, 905-921.
43 Ries-Kautt, M. (1999) in Protein Crystallization: Techniques, strategies and tips (Bergfors, T. M., ed.), pp. 93-110, International University Line, La Jolla, Calif.
44. Gilliland, G. L., Tung, M. and Ladner, J. E. (2002). The biological macromolecule crystallization database: crystallization procedures and strategies. Acta Crystallogr. D50, 916-920.
45. Vaney, M. C., Broutin, I., Retailleau, P., Douangamath, A., Lafont, S., Hamiaux, C., Prange, T., Ducruix, A. F. and Ries-Kautt, M. (2001). Structural effects of monovalent anions on polymorphic lysozyme crystals. Acta Crystallogr. D57, 929-940.
46. Lim, K., Nadarajah, A., Forsythe, E. L. and Pusey, M. L. (1998). Location of bromide ions in tetragonal lysozyme crystals. Acta Crystallogr. D54, 899-904.
47. Nicholls, A., Sharp, K. A. and Honig, B. (1991). Protein folding and association: insights from the interfacial and thermodynamic properties of hydrocarbons. Proteins Struct. Funct. Genet. 11, 281-296.
48. Kwong, P. D., Wyatt, R., Robinson, J., Sweet, R. W., Sodroski, J. and Hendrickson, W. A. (1998). Structure of an HIV gp120 envelope glycoprotein in complex with the CD4 receptor and a neutralizing human antibody. Nature 393, 648-659.
49. Wu, H., Kwong, P. D. and Hendrickson, W. A. (1997) Dimeric association and segmental variability in the structure of human CD4. Nature 387, 527-530.
50. Majeed, et al. (2003). Enhancing protein crystallization.

What is claimed is:

1. A method for screening reagents to identify a reagent in which a preselected compound forms a crystal, comprising the steps of:
   (a) separately contacting each of a plurality of reagents with the compound, wherein
      (i) each reagent is in a separate compartment;
      (ii) each reagent comprises a predetermined concentration of each of two types of precipitating agents selected from the group consisting of a first type of precipitating agent which alters the activity coefficient of water, a second type of precipitating agent which increases the molecular crowding of a compound in solution, and a third type of precipitating agent which reduces the dielectric of a solution solvating the compound, wherein for any reagent which contains the same two precipitating agents as one or more other reagents the concentration of at least one of the precipitating agents is different from the concentration of such precipitating agent in any such other reagent;
   (b) waiting a period of time up to a maximum of one year for a crystal to form in each such reagent if such a crystal will form in such reagent;
   (c) determining whether a crystal has formed in any of the reagents; and
   (d) identifying the reagent or reagents in which the crystal has formed,
so as to thereby identify the reagent or reagents in which the compound forms a crystal.

2. The method of claim 1, wherein the compound is a polypeptide.

3. The method of claim 2, wherein the polypeptide is a viral polypeptide.

4. The method of claim 3, wherein the viral polypeptide is an HIV polypeptide.

5. The method of claim 2, wherein the polypeptide is associated with a disease.

6. The method of claim 1, wherein the first type of precipitating agent is a salt.

7. The method of claim 6, wherein the salt is selected from the group consisting of $Am_2SO_4$, NaCl, $NaKPO_4$, AmCitrate, $Li_2SO_4$ and NaFormate.

8. The method of claim 1, wherein the second type of precipitating agent is PEG.

9. The method of claim 8, wherein the PEG is selected from the group consisting of PEG 3350, PEG 1500, PEG 8000 and PEG 4000.

10. The method of claim 1, wherein the third type of precipitating agent is an organic compound.

11. The method of claim 10, wherein the organic compound is selected from the group consisting of PEG 400, glycerol, MPD and isopropanol.

12. The method of claim 1, wherein the reagents have the same predetermined pH.

13. The method of claim 12, wherein the pH is between about 4.5 to about 8.5.

14. The method of claim 1, wherein the reagents comprise groups of reagents, wherein each group of reagents has a different predetermined pH.

15. The method of claim 14, wherein the reagents comprise two groups of reagents, the first group having a pH between about 4.5 to about 6.5, and the second group having a pH between about 6.5 to about 8.5.

16. The method of claim 14, wherein the reagents comprise four groups of reagents, the first group having a pH between about 4.5 to about 5.5, the second group having a pH between about 5.5 to about 6.5, the third group having a pH between about 6.5 to about 7.5, and the fourth group having a pH between about 7.5 to about 8.5.

17. The method of claim 1, wherein one or more reagents further comprises a salt selected from the group consisting of $MgSO_4$, $MgCl_2$, $CaCl_2$, $LiSO_4$, AmCitrate, $NaKPO_4$, $Am_2SO_4$ and NaCl.

18. The method of claim 1, wherein the reagents comprise eight distinct reagents.

19. The method of claim 1, wherein the reagents comprise 16 distinct reagents.

20. The method of claim 1, wherein the reagents comprise 32 distinct reagents.

21. The method of claim 1, wherein the reagents comprise 64 distinct reagents.

22. The method of claim 21, wherein the 64 reagents comprise the predetermined concentrations of the precipitating agents as listed in the following table:

| | Mechanism to enhance protein association | | |
|---|---|---|---|
| Reagent | (Salt) Alter the activity coefficient of water | (PEG) Increase molecular crowding | (Organic) Reduce the solvent dielectric |
| 1 | 2M $Am_2SO_4$ | | 2% PEG 400 |
| 2 | 2M $Am_2SO_4$ | | 10% Glycerol |
| 3 | 2M $Am_2SO_4$ | | 1% MPD |
| 4 | 2M $Am_2SO_4$ | | 5% PEG 400 |
| 5 | 4M NaCl | | 2% PEG 400 |
| 6 | 3M NaCl | | 5% MPD |
| 7 | 4M NaCl | | 5% Isopropanol |
| 8 | 2.5M $NaKPO_4$ | | 5% Isopropanol |
| 9 | 2M $NaKPO_4$ | | 2% PEG 400 |
| 10 | 2.5M $NaKPO_4$ | | 20% Glycerol |
| 11 | 1M $NaKPO_4$ | | 8% MPD |
| 12 | 2M AmCitrate | | 1% MPD |

-continued

Mechanism to enhance protein association

| Reagent | (Salt) Alter the activity coefficient of water crowding | (PEG) Increase molecular | (Organic) Reduce the solvent dielectric |
|---|---|---|---|
| 13 | 2M AmCitrate | | 5% Isopropanol |
| 14 | 2M AmCitrate | | 5% PEG 400 |
| 15 | 2M LiSO$_4$ | | 5% Isopropanol |
| 16 | 2M LiSO$_4$ | | 5% PEG 400 |
| 17 | 2M LiSO$_4$ | | 8% MPD |
| 18 | 2M LiSO$_4$ | | 2% PEG 400 |
| 19 | 1M LiSO$_4$ | | 15% MPD |
| 20 | 0.75M AmCitrate | | 25% MPD |
| 21 | 1.5M Am$_2$SO$_4$ | | 12% Isopropanol |
| 22 | 1.3M NaCl | | 30% Isopropanol |
| 23 | 4M NaCl | | 10% PEG 400 |
| 24 | 0.8M NaKPO$_4$ | | 20% PEG 400 |
| 25 | 1M AmCitrate | | 15% MPD |
| 26 | 2M NaFormate | 2.5% PEG 3350 | 15% Isopropanol |
| 27 | | 25% PEG 1500 | 30% MPD |
| 28 | | 15% PEG 8000 | 30% MPD |
| 29 | | 10% PEG 3350 | 30% MPD |
| 30 | | 4% PEG 1500 | 30% MPD |
| 31 | | 8% PEG 8000 | 30% MPD |
| 32 | | 4% PEG 3350 | 30% Isopropanol |
| 33 | | 10% PEG 1500 | 30% Isopropanol |
| 34 | | 15% PEG 8000 | 40% Isopropanol |
| 35 | | 15% PEG 3350 | 20% Isopropanol |
| 36 | | 30% PEG 3350 | 30% Isopropanol |
| 37 | | 20% PEG 8000 | 40% PEG 400 |
| 38 | | 5% PEG 3350 | 40% PEG 400 |
| 39 | | 15% PEG 1000 | 40% PEG 400 |
| 40 | | 8% PEG 8000 | 40% PEG 400 |
| 41 | | 20% PEG 3350 | 25% PEG 400 |
| 42 | | 30% PEG 1500 | 3% MPD |
| 43 | | 30% PEG 1500 | 10% Isopropanol |
| 44 | | 30% PEG 1500 | 20% PEG 400 |
| 45 | | 30% PEG 1500 | 8% MPD |
| 46 | | 25% PEG 3350 | 15% Isopropanol |
| 47 | | 25% PEG 3350 | 5% PEG 400 |
| 48 | | 25% PEG 3350 | 15% MPD |
| 49 | | 25% PEG 3350 | 4% Isopropanol |
| 50 | | 20% PEG 8000 | 10% PEG 400 |
| 51 | | 20% PEG 8000 | 3% MPD |
| 52 | | 20% PEG 8000 | 10% Isopropanol |
| 53 | | 20% PEG 8000 | 20% PEG 400 |
| 54 | 3M NaFormate | 25% PEG 3350 | |
| 55 | 0.75M Am$_2$SO$_4$ | 7.5% PEG 3350 | 5% Isopropanol |
| 56 | 1M AmCitrate | 1% PEG 4000 | |
| 57 | 2.5M NaCl | 12% PEG 1500 | 1.5% MPD |
| 58 | 3M NaCl | 20% PEG 3350 | |
| 59 | 3M NaFormate | 4% PEG 8000 | |
| 60 | 1M NaKPO$_4$ | 0.5% PEG 4000 | |
| 61 | 1.4M NaKPO$_4$ | 10% PEG 3350 | |
| 62 | 0.8M AmCitrate | 2% PEG 8000 | |
| 63 | 2M NaCl | 5% PEG 4000 | |
| 64 | 0.5M AmCitrate | 15% PEG 8000. | |

23. The method of claim 21, wherein the 64 reagents comprise the predetermined concentrations of the precipitating agents as listed in the following table:

| Reagent | Precipitating agents |
|---|---|
| 1 | 2000.000 mM (NH4)2 sulfate |
| | 2.000% v/v PEG-400 |
| 2 | 2000.000 mM (NH4)2 sulfate |
| | 10.000% v/v glycerol |
| 3 | 1.000% v/v MPD |
| | 2000.000 mM (NH4)2 sulfate |
| 4 | 2000.000 mM (NH4)2 sulfate |
| | 5.000% v/v PEG-400 |
| 5 | 3900.000 mM NaCl |
| | 2.000% v/v PEG-400 |
| 6 | 5.000% v/v MPD |
| | 3000.000 mM NaCl |
| 7 | 4000.000 mM NaCl |
| | 5.000% v/v isopropanol |
| 8 | 5.000% v/v isopropanol |
| 9 | 2.000% v/v PEG-400 |
| 10 | 20.000% v/v glycerol |
| 11 | 8.000% v/v MPD |
| 12 | 1.000% v/v MPD |
| 13 | 5.000% v/v isopropanol |
| 14 | 5.000% v/v PEG-400 |
| 15 | 5.000% v/v isopropanol |
| | 2000.000 mM Li2 sulfate |
| 16 | 2000.000 mM Li2 sulfate |
| | 5.000% v/v PEG-400 |
| 17 | 2000.000 mM Li2 sulfate |
| | 8.000% v/v MPD |
| 18 | 2000.000 mM Li2 sulfate |
| | 2.000% v/v PEG-400 |
| 19 | 15.000% v/v MPD |
| | 1000.000 mM Li2 sulfate |
| 20 | 25.000% v/v MPD |
| 21 | 1500.000 mM (NH4)2 sulfate |
| | 12.000% v/v isopropanol |
| 22 | 30.000% v/v isopropanol |
| | 1300.000 mM NaCl |
| 23 | 4000.000 mM NaCl |
| | 10.000% v/v PEG-400 |
| 24 | 20.000% v/v PEG-400 |
| 25 | 15.000% v/v isopropanol |
| 26 | 15.000% v/v isopropanol |
| | 2.500% w/v PEG-3350 |
| | 2000.000 mM Sodium formate |
| 27 | 30.000% v/v MPD |
| | 25.000% w/v PEG-1500 |
| 28 | 30.000% v/v MPD |
| | 15.000% w/v PEG-8000 |
| 29 | 30.000% v/v MPD |
| | 10.000% w/v PEG-3350 |
| 30 | 30.000% v/v MPD |
| | 4.000% w/v PEG-1500 |
| 31 | 30.000% v/v MPD |
| | 8.000% w/v PEG-8000 |
| 32 | 30.000% v/v isopropanol |
| | 4.000% w/v PEG-3350 |
| 33 | 10.000% w/v PEG-1500 |
| | 30.000% v/v isopropanol |
| 34 | 15.000% w/v PEG-8000 |
| | 40.000% v/v isopropanol |
| 35 | 20.000% v/v isopropanol |
| | 15.000% w/v PEG-3350 |
| 36 | 30.000% v/v isopropanol |
| | 30.000% w/v PEG-3350 |
| 37 | 20.000% w/v PEG-8000 |
| | 40.000% v/v PEG-400 |
| 38 | 40.000% v/v PEG-400 |
| | 5.000% w/v PEG-3350 |
| 39 | 15.000% w/v PEG-1000 |
| | 40.000% v/v PEG-400 |
| 40 | 8.000% w/v PEG-8000 |
| | 40.000% v/v PEG-400 |
| 41 | 25.000% v/v PEG-400 |
| | 20.000% w/v PEG-3350 |
| 42 | 3.000% v/v MPD |
| | 30.000% w/v PEG-1500 |
| 43 | 30.000% w/v PEG-1500 |
| | 10.000% v/v isopropanol |
| 44 | 30.000% w/v PEG-1500 |
| | 20.000% v/v PEG-400 |
| 45 | 8.000% v/v MPD |
| | 30.000% w/v PEG-1500 |
| 46 | 15.000% v/v isopropanol |
| | 25.000% w/v PEG-3350 |
| 47 | 5.000% v/v PEG-400 |
| | 5.000% w/v PEG-3350 |

| Reagent | Precipitating agents |
|---|---|
| 48 | 15.000% v/v MPD |
|  | 25.000% w/v PEG-3350 |
| 49 | 25.000% w/v PEG-3350 |
|  | 4.000% v/v isopropanol |
| 50 | 20.000% w/v PEG-8000 |
|  | 10.000% v/v PEG-400 |
| 51 | 3.000% v/v MPD |
|  | 20.000% w/v PEG-8000 |
| 52 | 20.000% w/v PEG-8000 |
|  | 10.000% v/v isopropanol |
| 53 | 20.000% w/v PEG-8000 |
|  | 20.000% v/v PEG-400 |
| 54 | 25.000% w/v PEG-3350 |
|  | 2100.000 mM Sodium formate |
| 55 | 750.000 mM (NH4)2 sulfate |
|  | 5.000% v/v isopropanol |
|  | 7.500% w/v PEG-3350 |
| 56 | 1.000% w/v PEG-4000 |
| 57 | 1.500% v/v MPD |
|  | 12.000% w/v PEG-1500 |
|  | 2500.000 mM NaCl |
| 58 | 2000.000 mM NaCl |
|  | 20.000% w/v PEG-3350 |
| 59 | 4.000% w/v PEG-8000 |
|  | 3000.000 mM Sodium formate |
| 60 | 0.500% w/v PEG-4000 |
| 61 | 10.000% w/v PEG-3350 |
| 62 | 2.000% w/v PEG-8000 |
| 63 | 5.000% w/v PEG-4000 |
|  | 2000.000 mM NaCl |
| 64 | 15.000% w/v PEG-8000. |

24. The method of claim 1, wherein the reagents comprise 128 distinct reagents.

25. The method of claim 1, wherein the reagents comprise 192 distinct reagents.

26. The method of claim 25, wherein the 192 reagents comprise the predetermined concentrations of the precipitating agents as listed in the following table:

| Reagent | Precipitating agents |
|---|---|
| 1 | 2000.000 mM (NH4)2 sulfate |
|  | 2.000% v/v PEG-400 |
| 2 | 2000.000 mM (NH4)2 sulfate |
|  | 10.000% v/v glycerol |
| 3 | 1.000% v/v MPD |
|  | 2000.000 mM (NH4)2 sulfate |
| 4 | 2000.000 mM (NH4)2 sulfate |
|  | 5.000% v/v PEG-400 |
| 5 | 3900.000 mM NaCl |
|  | 2.000% v/v PEG-400 |
| 6 | 5.000% v/v MPD |
|  | 3000.000 mM NaCl |
| 7 | 4000.000 mM NaCl |
|  | 5.000% v/v isopropanol |
| 8 | 5.000% v/v isopropanol |
| 9 | 2.000% v/v PEG-400 |
| 10 | 20.000% v/v glycerol |
| 11 | 8.000% v/v MPD |
| 12 | 1.000% v/v MPD |
| 13 | 5.000% v/v isopropanol |
| 14 | 5.000% v/v PEG-400 |
| 15 | 5.000% v/v isopropanol |
|  | 2000.000 mM Li2 sulfate |
| 16 | 2000.000 mM Li2 sulfate |
|  | 5.000% v/v PEG-400 |
| 17 | 2000.000 mM Li2 sulfate |
|  | 8.000% v/v MPD |
| 18 | 2000.000 mM Li2 sulfate |
|  | 2.000% v/v PEG-400 |
| 19 | 15.000% v/v MPD |
|  | 1000.000 mM Li2 sulfate |
| 20 | 25.000% v/v MPD |
| 21 | 1500.000 mM (NH4)2 sulfate |
|  | 12.000% v/v isopropanol |
| 22 | 30.000% v/v isopropanol |
|  | 1300.000 mM NaCl |
| 23 | 4000.000 mM NaCl |
|  | 10.000% v/v PEG-400 |
| 24 | 20.000% v/v PEG-400 |
| 25 | 15.000% v/v isopropanol |
| 26 | 15.000% v/v isopropanol |
|  | 2.500% w/v PEG-3350 |
|  | 2000.000 mM Sodium formate |
| 27 | 30.000% v/v MPD |
|  | 25.000% w/v PEG 1500 |
| 28 | 30.000% v/v MPD |
|  | 15.000% w/v PEG-8000 |
| 29 | 30.000% v/v MPD |
|  | 10.000% w/v PEG-3350 |
| 30 | 30.000% v/v MPD |
|  | 4.000% w/v PEG 1500 |
| 31 | 30.000% v/v MPD |
|  | 8.000% w/v PEG-8000 |
| 32 | 30.000% v/v isopropanol |
|  | 4.000% w/v PEG-3350 |
| 33 | 10.000% w/v PEG 1500 |
|  | 30.000% v/v isopropanol |
| 34 | 15.000% w/v PEG-8000 |
|  | 40.000% v/v isopropanol |
| 35 | 20.000% v/v isopropanol |
|  | 15.000% w/v PEG-3350 |
| 36 | 30.000% v/v isopropanol |
|  | 30.000% w/v PEG-3350 |
| 37 | 20.000% w/v PEG-8000 |
|  | 40.000% v/v PEG-400 |
| 38 | 40.000% v/v PEG-400 |
|  | 5.000% w/v PEG-3350 |
| 39 | 15.000% w/v PEG 1000 |
|  | 40.000% v/v PEG-400 |
| 40 | 8.000% w/v PEG-8000 |
|  | 40.000% v/v PEG-400 |
| 41 | 25.000% v/v PEG-400 |
|  | 20.000% w/v PEG-3350 |
| 42 | 3.000% v/v MPD |
|  | 30.000% w/v PEG 1500 |
| 43 | 30.000% w/v PEG 1500 |
|  | 10.000% v/v isopropanol |
| 44 | 30.000% w/v PEG 1500 |
|  | 20.000% v/v PEG-400 |
| 45 | 8.000% v/v MPD |
|  | 30.000% w/v PEG 1500 |
| 46 | 15.000% v/v isopropanol |
|  | 25.000% w/v PEG-3350 |
| 47 | 5.000% v/v PEG-400 |
|  | 25.000% w/v PEG-3350 |
| 48 | 15.000% v/v MPD |
|  | 25.000% w/v PEG-3350 |
| 49 | 25.000% w/v PEG-3350 |
|  | 4.000% v/v isopropanol |
| 50 | 20.000% w/v PEG-8000 |
|  | 10.000% v/v PEG-400 |
| 51 | 3.000% v/v MPD |
|  | 20.000% w/v PEG-8000 |
| 52 | 20.000% w/v PEG-8000 |
|  | 10.000% v/v isopropanol |
| 53 | 20.000% w/v PEG-8000 |
|  | 20.000% v/v PEG-400 |
| 54 | 25.000% w/v PEG-3350 |
|  | 2100.000 mM Sodium formate |
| 55 | 750.000 mM (NH4)2 sulfate |
|  | 5.000% v/v isopropanol |
|  | 7.500% w/v PEG-3350 |
| 56 | 1.000% w/v PEG-4000 |
| 57 | 1.500% v/v MPD |
|  | 12.000% w/v PEG-1500 |
|  | 2500.000 mM NaCl |

-continued

| Reagent | Precipitating agents |
|---|---|
| 58 | 2000.000 mM NaCl |
|  | 20.000% w/v PEG-3350 |
| 59 | 4.000% w/v PEG-8000 |
|  | 3000.000 mM Sodium formate |
| 60 | 0.500% w/v PEG-4000 |
| 61 | 10.000% w/v PEG-3350 |
| 62 | 2.000% w/v PEG-8000 |
| 63 | 5.000% w/v PEG-4000 |
|  | 2000.000 mM NaCl |
| 64 | 15.000% w/v PEG-8000 |
| 65 | 1340.000 mM (NH4)2 sulfate |
|  | 1.340% v/v PEG-400 |
| 66 | 1340.000 mM (NH4)2 sulfate |
|  | 6.700% v/v glycerol |
| 67 | .67000% v/v MPD |
|  | 1340.00 mM (NH4)2 sulfate |
| 68 | 1340.000 mM (NH4)2 sulfate |
|  | 3.350% v/v PEG-400 |
| 69 | 2613.000 mM NaCl |
|  | 1.340% v/v PEG-400 |
| 70 | 3.350% v/v MPD |
|  | 2010.00 mM NaCl |
| 71 | 2680.000 mM NaCl |
|  | 3.350% v/v isopropanol |
| 72 | 3.350% v/v isopropanol |
| 73 | 1.340% v/v PEG-400 |
| 74 | 13.400% v/v glycerol |
| 75 | 5.360% v/v MPD |
| 76 | .6700% v/v MPD |
| 77 | 3.350% v/v isopropanol |
| 78 | 3.350% v/v PEG-400 |
| 79 | 3.350% v/v isopropanol |
|  | 1340.00 mM Li2 sulfate |
| 80 | 1340.00 mM Li2 sulfate |
|  | 3.350% v/v PEG-400 |
| 81 | 1340.000 mM Li2 sulfate |
|  | 5.360% v/v MPD |
| 82 | 1340.00 mM Li2 sulfate |
|  | 1.340% v/v PEG-400 |
| 83 | 10.050% v/v MPD |
|  | 670.00 mM Li2 sulfate |
| 84 | 16.750% v/v MPD |
| 85 | 1005.00 mM (NH4)2 sulfate |
|  | 8.040% v/v isopropanol |
| 86 | 20.100% v/v isopropanol |
|  | 871.00 mM NaCl |
| 87 | 2680.000 mM NaCl |
|  | 6.700% v/v PEG-400 |
| 88 | 13.400% v/v PEG-400 |
| 89 | 10.050% v/v isopropanol |
| 90 | 10.050% v/v isopropanol |
|  | 1.6750% w/v PEG-3350 |
|  | 1340.00 mM Sodium formate |
| 91 | 20.100% v/v MPD |
|  | 16.750% w/v PEG 1500 |
| 92 | 20.100% v/v MPD |
|  | 10.050% w/v PEG-8000 |
| 93 | 20.100% v/v MPD |
|  | 6.700% w/v PEG-3350 |
| 94 | 20.100% v/v MPD |
|  | 2.680% w/v PEG 1500 |
| 95 | 20.100% v/v MPD |
|  | 5.360% w/v PEG-8000 |
| 96 | 20.100% v/v isopropanol |
|  | 2.680% w/v PEG-3350 |
| 97 | 6.700% w/v PEG 1500 |
|  | 20.100% v/v isopropanol |
| 98 | 10.0500% w/v PEG-8000 |
|  | 26.800% v/v isopropanol |
| 99 | 13.400% v/v isopropanol |
|  | 10.050% w/v PEG-3350 |
| 100 | 20.100% v/v isopropanol |
|  | 20.100% w/v PEG-3350 |
| 101 | 13.400% w/v PEG-8000 |
|  | 26.800% v/v PEG-400 |
| 102 | 26.800% v/v PEG-400 |
|  | 3.350% w/v PEG-3350 |
| 103 | 10.050% w/v PEG 1000 |
|  | 26.800% v/v PEG-400 |
| 104 | 5.360% w/v PEG-8000 |
|  | 26.000% v/v PEG-400 |
| 105 | 16.750% v/v PEG-400 |
|  | 13.400% w/v PEG-3350 |
| 106 | 2.010% v/v MPD |
|  | 20.100% w/v PEG 1500 |
| 107 | 20.100% w/v PEG 1500 |
|  | 6.700% v/v isopropanol |
| 108 | 20.100% w/v PEG 1500 |
|  | 13.400% v/v PEG-400 |
| 109 | 5.360% v/v MPD |
|  | 20.100% w/v PEG 1500 |
| 110 | 10.050% v/v isopropanol |
|  | 16.750% w/v PEG-3350 |
| 111 | 3.350% v/v PEG-400 |
|  | 16.750% w/v PEG-3350 |
| 112 | 10.050% v/v MPD |
|  | 16.750% w/v PEG-3350 |
| 113 | 16.750% w/v PEG-3350 |
|  | 2.680% v/v isopropanol |
| 114 | 13.400% w/v PEG-8000 |
|  | 6.700% v/v PEG-400 |
| 115 | 2.010% v/v MPD |
|  | 13.400% w/v PEG-8000 |
| 116 | 13.400% w/v PEG-8000 |
|  | 6.700% v/v isopropanol |
| 117 | 13.400% w/v PEG-8000 |
|  | 13.400% v/v PEG-400 |
| 118 | 16.750% w/v PEG-3350 |
|  | 1407.00 mM Sodium formate |
| 119 | 502.50 mM (NH4)2 sulfate |
|  | 3.350% v/v isopropanol |
|  | 7.500% w/v PEG-3350 |
| 120 | .6700% w/v PEG-4000 |
| 121 | 1.005% v/v MPD |
|  | 8.040% w/v PEG 1500 |
|  | 1675.00 mM NaCl |
| 122 | 13.400% w/v PEG-3350 |
|  | 1340.000 mM NaCl |
| 123 | 2.680% w/v PEG-8000 |
|  | 2010.00 mM Sodium formate |
| 124 | .3350% w/v PEG-4000 |
| 125 | 6.700% w/v PEG-3350 |
| 126 | 1.340% w/v PEG-8000 |
| 127 | 3.350% w/v PEG-4000 |
|  | 1340.00 mM NaCl |
| 128 | 10.050% w/v PEG-8000 |
| 129 | 660.00 mM (NH4)2 sulfate |
|  | .660% v/v PEG-400 |
| 130 | 660.000 mM (NH4)2 sulfate |
|  | 3.300% v/v glycerol |
| 131 | .330% v/v MPD |
|  | 660.00 mM (NH4)2 sulfate |
| 132 | 660.00 mM (NH4)2 sulfate |
|  | 1.650% v/v PEG-400 |
| 133 | 1287.000 mM NaCl |
|  | .660% v/v PEG-400 |
| 134 | 1.650% v/v MPD |
|  | 990.000 mM NaCl |
| 135 | 1.650% v/v isopropanol |
|  | 1320.000 mM NaCl |
| 136 | 1.650% v/v isopropanol |
| 137 | .660% v/v PEG-400 |
| 138 | 6.600% v/v glycerol |
| 139 | 2.640% v/v MPD |
| 140 | .330% v/v MPD |
| 141 | 1.650% v/v isopropanol |
| 142 | 1.650% v/v PEG-400 |
| 143 | 1.650% v/v isopropanol |
|  | 660.000 mM Li2 sulfate |
| 144 | 660.000 mM Li2 sulfate |
|  | 1.650% v/v PEG-400 |
| 145 | 660.000 mM Li2 sulfate |
|  | 2.640% v/v MPD |

| Reagent | Precipitating agents |
|---|---|
| 146 | 660.000 mM Li2 sulfate |
|  | .660% v/v PEG-400 |
| 147 | 4.950% v/v MPD |
|  | 330.000 mM Li2 sulfate |
| 148 | 8.250% v/v MPD |
| 149 | 495.000 mM (NH4)2 sulfate |
|  | 3.960% v/v isopropanol |
| 150 | 9.900% v/v isopropanol |
|  | 429.000 mM NaCl |
| 151 | 1320.000 mM NaCl |
|  | 3.300% v/v PEG-400 |
| 152 | 6.600% v/v PEG-400 |
| 153 | 4.950% v/v isopropanol |
| 154 | 4.950% v/v isopropanol |
|  | 0.825% w/v PEG-3350 |
|  | 660.000 mM Sodium formate |
| 155 | 9.900% v/v MPD |
|  | 8.250% w/v PEG 1500 |
| 156 | 9.900% v/v MPD |
|  | 4.950% w/v PEG-8000 |
| 157 | 9.900% v/v MPD |
|  | 3.300% w/v PEG-3350 |
| 158 | 9.900% v/v MPD |
|  | 1.320% w/v PEG 1500 |
| 159 | 9.900% v/v MPD |
|  | 2.640% w/v PEG-8000 |
| 160 | 9.900% v/v isopropanol |
|  | 1.320% w/v PEG-3350 |
| 161 | 3.300% w/v PEG 1500 |
|  | 9.900% v/v isopropanol |
| 162 | 4.950% w/v PEG-8000 |
|  | 13.20% v/v isopropanol |
| 163 | 6.600% v/v isopropanol |
|  | 4.950% w/v PEG-3350 |
| 164 | 9.900% v/v isopropanol |
|  | 9.900% w/v PEG-3350 |
| 165 | 6.600% w/v PEG-8000 |
|  | 13.200% v/v PEG-400 |
| 166 | 13.200% v/v PEG-400 |
|  | 1.650% w/v PEG-3350 |
| 167 | 4.950% w/v PEG 1000 |
|  | 13.20% v/v PEG-400 |
| 168 | 2.640% w/v PEG-8000 |
|  | 13.20% v/v PEG-400 |
| 169 | 8.250% v/v PEG-400 |
|  | 6.600% w/v PEG-3350 |
| 170 | .990% v/v MPD |
|  | 9.900% w/v PEG 1500 |
| 171 | 9.900% w/v PEG 1500 |
|  | 3.300% v/v isopropanol |
| 172 | 9.900% w/v PEG 1500 |
|  | 6.600% v/v PEG-400 |
| 173 | 2.640% v/v MPD |
|  | 9.900% w/v PEG 1500 |
| 174 | 4.950% v/v isopropanol |
|  | 8.250% w/v PEG-3350 |
| 175 | 1.650% v/v PEG-400 |
|  | 8.250% w/v PEG-3350 |
| 176 | 4.950% v/v MPD |
|  | 8.250% w/v PEG-3350 |
| 177 | 8.250% w/v PEG-3350 |
|  | 1.320% v/v isopropanol |
| 178 | 6.600% w/v PEG-8000 |
|  | 3.300% v/v PEG-400 |
| 179 | .990% v/v MPD |
|  | 6.60% w/v PEG-8000 |
| 180 | 6.600% w/v PEG-8000 |
|  | 3.300% v/v isopropanol |
| 181 | 6.600% w/v PEG-8000 |
|  | 6.600% w/v PEG-400 |
| 182 | 8.250% w/v PEG-3350 |
|  | 693.000 mM Sodium formate |
| 183 | 247.500 mM (NH4)2 sulfate |
|  | 1.650% v/v isopropanol |
|  | 2.475% w/v PEG-3350 |
| 184 | 0.330% w/v PEG-4000 |
| 185 | .495% v/v MPD |
|  | 3.960% w/v PEG 1500 |
|  | 825.000 mM NaCl |
| 186 | 660.000 mM NaCl |
|  | 6.600% w/v PEG-3350 |
| 187 | 1.320% w/v PEG-8000 |
|  | 990.000 mM Sodium formate |
| 188 | 0.165% w/v PEG-4000 |
| 189 | 3.300% w/v PEG-3350 |
| 190 | 0.660% w/v PEG-8000 |
| 191 | 1.650% w/v PEG-4000 |
|  | 2000.000 mM NaCl |
| 192 | 4.950% w/v PEG-8000. |

27. The method of claim 1, wherein the method is performed, at least in part, using an automated system.

28. The method of claim 1, wherein the compound is known to crystallize in one reagent.

29. A method for crystallizing a preselected compound comprising contacting the compound with a reagent for a period of time up to a maximum of one year, wherein the reagent has been identified according to the method of claim 1.

30. A kit for use in identifying a reagent in which a preselected compound crystallizes, comprising a plurality of reagents wherein
   (i) each reagent, is in a separate compartment;
   (ii) each reagent comprises a predetermined concentration of each of two types of precipitating agents selected from the group consisting of a first type of precipitating agent which alters the activity coefficient of water, a second type of precipitating agent which increases the molecular crowding of a compound in solution, and a third type of precipitating agent which reduces the dielectric of a solution solvating the compound, wherein for any reagent which contains the same two precipitating agents as one or more other reagents the concentration of at least one of the precipitating agents is different from the concentration of such precipitating agent in any such other reagent.

31. The kit of claim 30, further comprising instructions for use.

32. The kit of claim 30, wherein the reagents are contained in (i) one or a plurality of well-containing plates suitable for use in growing crystals, whereby each reagent is contained within a discrete well, or (ii) a plurality of conical tubes suitable for use in growing crystals, whereby each tube contains a single reagent.

33. The kit of claim 32, wherein the reagents are contained in one well-containing plate suitable for use in growing crystals.

34. The kit of claim 32, wherein the reagents are contained in a plurality of well-containing plates suitable for use in growing crystals.

35. The kit of claim 32, wherein the reagents are contained in a plurality of conical tubes suitable for use in growing crystals.

36. The kit of claim 32, wherein the well-containing plates are suitable for use in an automated system.

37. The kit of claim 30, wherein the first type of precipitating agent is a salt.

38. The kit of claim 37, wherein the salt is selected from the group consisting of $Am_2SO_4$, NaCl, $NaKPO_4$, AmCitrate, $Li_2SO_4$ and NaFormate.

39. The kit of claim 30, wherein the second type of precipitating agent is PEG.

40. The kit of claim 39, wherein the PEG is selected from the group consisting of PEG 3350, PEG 1500, PEG 8000 and PEG 4000.

41. The kit of claim 30, wherein the third type of precipitating agent is an organic compound.

42. The kit of claim 41, wherein the organic compound is selected from the group consisting of PEG 400, glycerol, MPD and isopropanol.

43. The kit of claim 30, wherein the reagents have the same predetermined pH.

44. The kit of claim 43, wherein the pH is between about 4.5 to about 8.5.

45. The kit of claim 30, wherein the reagents comprise groups of reagents, wherein each group of reagents has a different predetermined pH.

46. The kit of claim 45, wherein the reagents comprise two groups of reagents, the first group having a pH between about 4.5 to about 6.5, and the second group having a pH between about 6.5 to about 8.5.

47. The kit of claim 45, wherein the reagents comprise four groups, the first group having a pH between about 4.5 to about 5.5, the second group having a pH between about 5.5 to about 6.5, the third group having a pH between about 6.5 to about 7.5, and the fourth group having a pH between about 7.5 to about 8.5.

48. The kit of claim 30, wherein one or more reagents further comprises a salt selected from the group consisting of $MgSO_4$, $MgCl_2$, $CaCl_2$, $LiSO_4$, Amditrate, $NaKPO_4$, $Am_2SO_4$ and NaCl.

49. The kit of claim 30, wherein the plurality of reagents comprise eight distinct reagents.

50. The kit of claim 30, wherein the reagents comprise 16 distinct reagents.

51. The kit of claim 30, wherein the reagents comprise 32 distinct reagents.

52. The kit of claim 30, wherein the reagents comprise 64 distinct reagents.

53. The kit of claim 52, wherein the 64 reagents comprise the predetermined concentrations of the precipitating agents as listed in the following table:

| | Mechanism to enhance protein association | | |
| --- | --- | --- | --- |
| Reagent | (Salt) Alter the activity coefficient of water crowding | (PEG-) Increase molecular | (Organic) Reduce the solvent dielectric |
| 1 | 2 M $Am_2SO_4$ | | 2% PEG 400 |
| 2 | 2 M $Am_2SO_4$ | | 10% Glycerol |
| 3 | 2 M $Am_2SO_4$ | | 1% MPD |
| 4 | 2 M $Am_2SO_4$ | | 5% PEG 400 |
| 5 | 4 M NaCl | | 2% PEG 400 |
| 6 | 3 M NaCl | | 5% MPD |
| 7 | 4 M NaCl | | 5% Isopropanol |
| 8 | 2.5 M $NaKPO_4$ | | 5% Isopropanol |
| 9 | 2 M $NaKPO_4$ | | 2% PEG 400 |
| 10 | 2.5 M $NaKPO_4$ | | 20% Glycerol |
| 11 | 1 M $NaKPO_4$ | | 8% MPD |
| 12 | 2 M AmCitrate | | 1% MPD |
| 13 | 2 M AmCitrate | | 5% Isopropanol |
| 14 | 2 M AmCitrate | | 5% PEG 400 |
| 15 | 2 M $LiSO_4$ | | 5% Isopropanol |
| 16 | 2 M $LiSO_4$ | | 5% PEG 400 |
| 17 | 2 M $LiSO_4$ | | 8% MPD |
| 18 | 2 M $LiSO_4$ | | 2% PEG 400 |
| 19 | 1 M $LiSO_4$ | | 15% MPD |
| 20 | 0.75 M AmCitrate | | 25% MPD |
| 21 | 1.5 M $Am_2SO_4$ | | 12% Isopropanol |
| 22 | 1.3 M NaCl | | 30% Isopropanol |
| 23 | 4 M NaCl | | 10% PEG 400 |
| 24 | 0.8 M $NaKPO_4$ | | 20% PEG 400 |
| 25 | 1 M AmCitrate | | 15% Isopropanol |
| 26 | 2 M NaFormate | 2.5% PEG 3350 | 15% Isopropanol |
| 27 | | 25% PEG 1500 | 30% MPD |
| 28 | | 15% PEG 8000 | 30% MPD |
| 29 | | 10% PEG 3350 | 30% MPD |
| 30 | | 4% PEG 1500 | 30% MPD |
| 31 | | 8% PEG 8000 | 30% MPD |
| 32 | | 4% PEG 3350 | 30% Isopropanol |
| 33 | | 10% PEG 1500 | 30% Isopropanol |
| 34 | | 15% PEG 8000 | 40% Isopropanol |
| 35 | | 15% PEG 3350 | 20% Isopropanol |
| 36 | | 30% PEG 3350 | 30% Isopropanol |
| 37 | | 20% PEG 8000 | 40% PEG 400 |
| 38 | | 5% PEG 3350 | 40% PEG 400 |
| 39 | | 15% PEG 1000 | 40% PEG 400 |
| 40 | | 8% PEG 8000 | 40% PEG 400 |
| 41 | | 20% PEG 3350 | 25% PEG 400 |
| 42 | | 30% PEG 1500 | 3% MPD |
| 43 | | 30% PEG 1500 | 10% Isopropanol |
| 44 | | 30% PEG 1500 | 20% PEG 400 |
| 45 | | 30% PEG 1500 | 8% MPD |
| 46 | | 25% PEG 3350 | 15% Isopropanol |
| 47 | | 25% PEG 3350 | 5% PEG 400 |
| 48 | | 25% PEG 3350 | 15% MPD |
| 49 | | 25% PEG 3350 | 4% Isopropanol |
| 50 | | 20% PEG 8000 | 10% PEG 400 |
| 51 | | 20% PEG 8000 | 3% MPD |
| 52 | | 20% PEG 8000 | 10% Isopropanol |
| 53 | | 20% PEG 8000 | 20% PEG 400 |
| 54 | 3 M NaFormate | 25% PEG 3350 | |
| 55 | 0.75 M $Am_2SO_4$ | 7.5% PEG 3350 | 5% Isopropanol |
| 56 | 1 M AmCitrate | 1% PEG 4000 | |
| 57 | 2.5 M NaCl | 12% PEG 1500 | 1.5% MPD |
| 58 | 3 M NaCl | 20% PEG 3350 | |
| 59 | 3 M NaFormate | 4% PEG 8000 | |
| 60 | 1 M $NaKPO_4$ | 0.5% PEG 4000 | |
| 61 | 1.4 M $NaKPO_4$ | 10% PEG 3350 | |
| 62 | 0.8 M AmCitrate | 2% PEG 8000 | |
| 63 | 2 M NaCl | 5% PEG 4000 | |
| 64 | 0.5 M AmCitrate | 15% PEG 8000. | |

54. The kit of claim 52, wherein the 64 reagents comprise the predetermined concentrations of the precipitating agents as listed in the following table:

| Reagent | Precipitating agents |
| --- | --- |
| 1 | 2000.000 mM (NH4)2 sulfate 2.000% v/v PEG-400 |
| 2 | 2000.000 mM (NH4)2 sulfate 10.000% v/v glycerol |

-continued

| Reagent | Precipitating agents |
|---|---|
| 3 | 1.000% v/v MPD |
|   | 2000.000 mM (NH4)2 sulfate |
| 4 | 2000.000 mM (NH4)2 sulfate |
|   | 5.000% v/v PEG-400 |
| 5 | 3900.000 mM NaCl |
|   | 2.000% v/v PEG-400 |
| 6 | 5.000% v/v MPD |
|   | 3000.000 mM NaCl |
| 7 | 4000.000 mM NaCl |
|   | 5.000% v/v isopropanol |
| 8 | 5.000% v/v isopropanol |
| 9 | 2.000% v/v PEG-400 |
| 10 | 20.000% v/v glycerol |
| 11 | 8.000% v/v MPD |
| 12 | 1.000% v/v MPD |
| 13 | 5.000% v/v isopropanol |
| 14 | 5.000% v/v PEG-400 |
| 15 | 5.000% v/v isopropanol |
|   | 2000.000 mM Li2 sulfate |
| 16 | 2000.000 mM Li2 sulfate |
|   | 5.000% v/v PEG-400 |
| 17 | 2000.000 mM Li2 sulfate |
|   | 8.000% v/v MPD |
| 18 | 2000.000 mM Li2 sulfate |
|   | 2.000% v/v PEG-400 |
| 19 | 15.000% v/v MPD |
|   | 1000.000 mM Li2 sulfate |
| 20 | 25.000% v/v MPD |
| 21 | 1500.000 mM (NH4)2 sulfate |
|   | 12.000% v/v isopropanol |
| 22 | 30.000% v/v isopropanol |
|   | 1300.000 mM NaCl |
| 23 | 4000.000 mM NaCl |
|   | 10.000% v/v PEG-400 |
| 24 | 20.000% v/v PEG-400 |
| 25 | 15.000% v/v isopropanol |
|   | 15.000% v/v isopropanol |
| 26 | 2.500% w/v PEG-3350 |
|   | 2000.000 mM Sodium formate |
| 27 | 30.000% v/v MPD |
|   | 25.000% w/v PEG 1500 |
| 28 | 30.000% v/v MPD |
|   | 15.000% w/v PEG-8000 |
| 29 | 30.000% v/v MPD |
|   | 10.000% w/v PEG-3350 |
| 30 | 30.000% v/v MPD |
|   | 4.000% w/v PEG 1500 |
| 31 | 30.000% v/v MPD |
|   | 8.000% w/v PEG-8000 |
| 32 | 30.000% v/v isopropanol |
|   | 4.000% w/v PEG-3350 |
| 33 | 10.000% w/v PEG 1500 |
|   | 30.000% v/v isopropanol |
| 34 | 15.000% w/v PEG-8000 |
|   | 40.000% v/v isopropanol |
| 35 | 20.000% v/v isopropanol |
|   | 15.000% w/v PEG-3350 |
| 36 | 30.000% v/v isopropanol |
|   | 30.000% w/v PEG-3350 |
| 37 | 20.000% w/v PEG-8000 |
|   | 40.000% v/v PEG-400 |
| 38 | 40.000% v/v PEG-400 |
|   | 5.000% w/v PEG-3350 |
| 39 | 15.000% w/v PEG 1000 |
|   | 40.000% v/v PEG-400 |
| 40 | 8.000% w/v PEG-8000 |
|   | 40.000% v/v PEG-400 |
| 41 | 25.000% v/v PEG-400 |
|   | 20.000% w/v PEG-3350 |
| 42 | 3.000% v/v MPD |
|   | 30.000% w/v PEG 1500 |
| 43 | 30.000% w/v PEG 1500 |
|   | 10.000% v/v isopropanol |
| 44 | 30.000% w/v PEG 1500 |
|   | 20.000% v/v PEG-400 |
| 45 | 8.000% v/v MPD |
|   | 30.000% w/v PEG 1500 |

-continued

| Reagent | Precipitating agents |
|---|---|
| 46 | 15.000% v/v isopropanol |
|   | 25.000% w/v PEG-3350 |
| 47 | 5.000% v/v PEG-400 |
|   | 5.000% w/v PEG-3350 |
| 48 | 15.000% v/v MPD |
|   | 25.000% w/v PEG-3350 |
| 49 | 25.000% w/v PEG-3350 |
|   | 4.000% v/v isopropanol |
| 50 | 20.000% w/v PEG-8000 |
|   | 10.000% v/v PEG-400 |
| 51 | 3.000% v/v MPD |
|   | 20.000% w/v PEG-8000 |
| 52 | 20.000% w/v PEG-8000 |
|   | 10.000% v/v isopropanol |
| 53 | 20.000% w/v PEG-8000 |
|   | 20.000% v/v PEG-400 |
| 54 | 25.000% w/v PEG-3350 |
|   | 2100.000 mM Sodium formate |
| 55 | 750.000 mM (NH4)2 sulfate |
|   | 5.000% v/v isopropanol |
|   | 7.500% w/v PEG-3350 |
| 56 | 1.000% w/v PEG-4000 |
| 57 | 1.500% v/v MPD |
|   | 12.000% w/v PEG 1500 |
|   | 2500.000 mM NaCl |
| 58 | 2000.000 mM NaCl |
|   | 20.000% w/v PEG-3350 |
|   | 4.000% w/v PEG-8000 |
|   | 3000.000 mM Sodium formate |
| 60 | 0.500% w/v PEG-4000 |
| 61 | 10.000% w/v PEG-3350 |
| 62 | 2.000% w/v PEG-8000 |
| 63 | 5.000% w/v PEG-4000 |
|   | 2000.000 mM NaCl |
| 64 | 15.000% w/v PEG-8000. |

55. The kit of claim 30, wherein the reagents comprise 128 distinct reagents.

56. The kit of claim 30, wherein the reagents comprise 132 distinct reagents.

57. The kit of claim 56, wherein the 132 reagents comprise the predetermined concentrations of the precipitating agents as listed in the following tab:

| Reagent | Precipitating agents |
|---|---|
| 1 | 2000.000 mM (NH4)2 sulfate |
|   | 2.000% v/v PEG-400 |
| 2 | 2000.000 mM (NH4)2 sulfate |
|   | 10.000% v/v glycerol |
| 3 | 1.000% v/v MPD |
|   | 2000.000 mM (NH4)2 sulfate |
| 4 | 2000.000 mM (NH4)2 sulfate |
|   | 5.000% v/v PEG-400 |
| 5 | 3900.000 mM NaCl |
|   | 2.000% v/v PEG-400 |
| 6 | 5.000% v/v MPD |
|   | 3000.000 mM NaCl |
| 7 | 4000.000 mM NaCl |
|   | 5.000% v/v isopropanol |
| 8 | 5.000% v/v isopropanol |
| 9 | 2.000% v/v PEG-400 |
| 10 | 20.000% v/v glycerol |
| 11 | 8.000% v/v MPD |
| 12 | 1.000% v/v MPD |
| 13 | 5.000% v/v isopropanol |
| 14 | 5.000% v/v PEG-400 |
| 15 | 5.000% v/v isopropanol |
|   | 2000.000 mM Li2 sulfate |
| 16 | 2000.000 mM Li2 sulfate |
|   | 5.000% v/v PEG-400 |

-continued

| Reagent | Precipitating agents |
|---|---|
| 17 | 2000.000 mM Li2 sulfate |
|  | 8.000% v/v MPD |
| 18 | 2000.000 mM Li2 sulfate |
|  | 2.000% v/v PEG-400 |
| 19 | 15.000% v/v MPD |
|  | 1000.000 mM Li2 sulfate |
| 20 | 25.000% v/v MPD |
| 21 | 1500.000 mM (NH4)2 sulfate |
|  | 12.000% v/v isopropanol |
| 22 | 30.000% v/v isopropanol |
|  | 1300.000 mM NaCl |
| 23 | 4000.000 mM NaCl |
|  | 10.000% v/v PEG-400 |
| 24 | 20.000% v/v PEG-400 |
| 25 | 15.000% v/v isopropanol |
| 26 | 15.000% v/v isopropanol |
|  | 2.500% w/v PEG-3350 |
|  | 2000.000 mM Sodium formate |
| 27 | 30.000% v/v MPD |
|  | 25.000% w/v PEG 1500 |
| 28 | 30.000% v/v MPD |
|  | 15.000% w/v PEG-8000 |
| 29 | 30.000% v/v MPD |
|  | 10.000% w/v PEG-3350 |
| 30 | 30.000% v/v MPD |
|  | 4.000% w/v PEG 1500 |
| 31 | 30.000% v/v MPD |
|  | 8.000% w/v PEG-8000 |
| 32 | 30.000% v/v isopropanol |
|  | 4.000% w/v PEG-3350 |
| 33 | 10.000% w/v PEG 1500 |
|  | 30.000% v/v isopropanol |
| 34 | 15.000% w/v PEG-8000 |
|  | 40.000% v/v isopropanol |
| 35 | 20.000% v/v isopropanol |
|  | 15.000% w/v PEG-3350 |
| 36 | 30.000% v/v isopropanol |
|  | 30.000% w/v PEG-3350 |
| 37 | 20.000% w/v PEG-8000 |
|  | 40.000% v/v PEG-400 |
| 38 | 40.000% v/v PEG-400 |
|  | 5.000% w/v PEG-3350 |
| 39 | 15.000% w/v PEG 1000 |
|  | 40.000% v/v PEG-400 |
| 40 | 8.000% w/v PEG-8000 |
|  | 40.000% v/v PEG-400 |
| 41 | 25.000% v/v PEG-400 |
|  | 20.000% w/v PEG-3350 |
| 42 | 3.000% v/v MPD |
|  | 30.000% w/v PEG 1500 |
| 43 | 30.000% w/v PEG 1500 |
|  | 10.000% v/v isopropanol |
| 44 | 30.000% w/v PEG 1500 |
|  | 20.000% v/v PEG-400 |
| 45 | 8.000% v/v MPD |
|  | 30.000% w/v PEG 1500 |
| 46 | 15.000% v/v isopropanol |
|  | 25.000% w/v PEG-3350 |
| 47 | 5.000% v/v PEG-400 |
|  | 25.000% w/v PEG-3350 |
| 48 | 15.000% v/v MPD |
|  | 25.000% w/v PEG-3350 |
| 49 | 25.000% w/v PEG-3350 |
|  | 4.000% v/v isopropanol |
| 50 | 20.000% w/v PEG-8000 |
|  | 10.000% v/v PEG-400 |
| 51 | 3.000% v/v MPD |
|  | 20.000% w/v PEG-8000 |
| 52 | 20.000% w/v PEG-8000 |
|  | 10.000% v/v isopropanol |
| 53 | 20.000% w/v PEG-8000 |
|  | 20.000% v/v PEG-400 |
| 54 | 25.000% w/v PEG-3350 |
|  | 2100.000 mM Sodium formate |
| 55 | 750.000 mM (NH4)2 sulfate |
|  | 5.000% v/v isopropanol |
|  | 7.500% v/v PEG-3350 |
| 56 | 1.000% w/v PEG-4000 |
| 57 | 1.500% v/v MPD |
|  | 12.000% w/v PEG 1500 |
|  | 2500.000 mM NaCl |
| 58 | 2000.000 mM NaCl |
|  | 20.000% w/v PEG-3350 |
| 59 | 4.000% w/v PEG-8000 |
|  | 3000.000 mM Sodium formate |
| 60 | 0.500% w/v PEG-4000 |
| 61 | 10.000% w/v PEG-3350 |
| 62 | 2.000% w/v PEG-8000 |
| 63 | 5.000% w/v PEG-4000 |
|  | 2000.000 mM NaCl |
| 64 | 15.000% w/v PEG-8000 |
| 65 | 1340.000 mM (NH4)2 sulfate |
|  | 1.340% v/v PEG-400 |
| 66 | 1340.000 mM (NH4)2 sulfate |
|  | 6.700% v/v glycerol |
| 67 | .67000% v/v MPD |
|  | 1340.00 mM (NH4)2 sulfate |
| 68 | 1340.000 mM (NH4)2 sulfate |
|  | 3.350% v/v PEG-400 |
| 69 | 2613.000 mM NaCl |
|  | 1.340% v/v PEG-400 |
| 70 | 3.350% v/v MPD |
|  | 2010.00 mM NaCl |
| 71 | 2680.000 mM NaCl |
|  | 3.350% v/v isopropanol |
| 72 | 3.350% v/v isopropanol |
| 73 | 1.340% v/v PEG-400 |
| 74 | 13.400% v/v glycerol |
| 75 | 5.360% v/v MPD |
| 76 | .6700% v/v MPD |
| 77 | 3.350% v/v isopropanol |
| 78 | 3.350% v/v PEG-400 |
| 79 | 3.350% v/v isopropanol |
|  | 1340.00 mM Li2 sulfate |
| 80 | 1340.00 mM Li2 sulfate |
|  | 3.350% v/v PEG-400 |
| 81 | 1340.000 mM Li2 sulfate |
|  | 5.360% v/v MPD |
| 82 | 1340.00 mM Li2 sulfate |
|  | 1.340% v/v PEG-400 |
| 83 | 10.050% v/v MPD |
|  | 670.00 mM Li2 sulfate |
| 84 | 16.750% v/v MPD |
| 85 | 1005.00 mM (NH4)2 sulfate |
|  | 8.040% v/v isopropanol |
| 86 | 20.100% v/v isopropanol |
|  | 871.00 mM NaCl |
| 87 | 2680.000 mM NaCl |
|  | 6.700% v/v PEG-400 |
| 88 | 13.400% v/v PEG-400 |
| 89 | 10.050% v/v isopropanol |
| 90 | 10.050% v/v isopropanol |
|  | 1.6750% w/v PEG-3350 |
|  | 1340.00 mM Sodium formate |
| 91 | 20.100% v/v MPD |
|  | 16.750% w/v PEG 1500 |
| 92 | 20.100% v/v MPD |
|  | 10.050% w/v PEG-8000 |
| 93 | 20.100% v/v MPD |
|  | 6.700% w/v PEG-3350 |
| 94 | 20.100% v/v MPD |
|  | 2.680% w/v PEG 1500 |
| 95 | 20.100% v/v MPD |
|  | 5.360% w/v PEG-8000 |
| 96 | 20.100% v/v isopropanol |
|  | 2.680% w/v PEG-3350 |
| 97 | 6.700% w/v PEG 1500 |
|  | 20.100% v/v isopropanol |
| 98 | 10.0500% w/v PEG-8000 |
|  | 26.800% v/v isopropanol |
| 99 | 13.400% v/v isopropanol |
|  | 10.050% w/v PEG-3350 |
| 100 | 20.100% v/v isopropanol |
|  | 20.100% w/v PEG-3350 |

-continued

| Reagent | Precipitating agents |
|---|---|
| 101 | 13.400% w/v PEG-8000 |
|  | 26.800% v/v PEG-400 |
| 102 | 26.800% v/v PEG-400 |
|  | 3.350% w/v PEG-3350 |
| 103 | 10.050% w/v PEG 1000 |
|  | 26.800% v/v PEG-400 |
| 104 | 5.360% w/v PEG-8000 |
|  | 26.800% v/v PEG-400 |
| 105 | 16.750% v/v PEG-400 |
|  | 13.400% w/v PEG-3350 |
| 106 | 2.010% v/v MPD |
|  | 20.100% w/v PEG 1500 |
| 107 | 20.100% w/v PEG 1500 |
|  | 6.700% v/v isopropanol |
| 108 | 20.100% w/v PEG 1500 |
|  | 13.400% v/v PEG-400 |
| 109 | 5.360% v/v MPD |
|  | 20.100% w/v PEG 1500 |
| 110 | 10.050% v/v isopropanol |
|  | 16.750% w/v PEG-3350 |
| 111 | 3.350% v/v PEG-400 |
|  | 16.750% w/v PEG-3350 |
| 112 | 10.050% v/v MPD |
|  | 16.750% w/v PEG-3350 |
| 113 | 16.750% w/v PEG-3350 |
|  | 2.680% v/v isopropanol |
| 114 | 13.400% w/v PEG-8000 |
|  | 6.700% v/v PEG-400 |
| 115 | 2.010% v/v MPD |
|  | 13.400% w/v PEG-8000 |
| 116 | 13.400% w/v PEG-8000 |
|  | 6.700% v/v isopropanol |
| 117 | 13.400% w/v PEG-8000 |
|  | 13.400% v/v PEG-400 |
| 118 | 16.750% w/v PEG-3350 |
|  | 1407.00 mM Sodium formate |
| 119 | 502.50 mM (NH4)2 sulfate |
|  | 3.350% v/v isopropanol |
|  | 7.500% w/v PEG-3350 |
| 120 | .6700% w/v PEG-4000 |
| 121 | 1.005% v/v MPD |
|  | 8.040% w/v PEG 1500 |
|  | 1675.00 mM NaCl |
| 122 | 13.400% w/v PEG-3350 |
|  | 1340.000 mM NaCl |
| 123 | 2.680% w/v PEG-8000 |
|  | 2010.00 mM Sodium formate |
| 124 | .3350% w/v PEG-4000 |
| 125 | 6.700% w/v PEG-3350 |
| 126 | 1.340% w/v PEG-8000 |
| 127 | 3.350% w/v PEG-4000 |
|  | 1340.00 mM NaCl |
| 128 | 10.050% w/v PEG-8000 |
| 129 | 660.00 mM (NH4)2 sulfate |
|  | .660% v/v PEG-400 |
| 130 | 660.000 mM (NH4)2 sulfate |
|  | 3.300% v/v glycerol |
| 131 | .330% v/v MPD |
|  | 660.00 mM (NH4)2 sulfate |
| 132 | 660.000 mM (NH4)2 sulfate |
|  | 1.650% v/v PEG-400 |
| 133 | 1287.000 mM NaCl |
|  | .660% v/v PEG-400 |
| 134 | 1.650% v/v MPD |
|  | 990.000 mM NaCl |
| 135 | 1.650% v/v isopropanol |
|  | 1320.000 mM NaCl |
| 136 | 1.650% v/v isopropanol |
| 137 | .660% v/v PEG-400 |
| 138 | 6.600% v/v glycerol |
| 139 | 2.640% v/v MPD |
| 140 | .330% v/v MPD |
| 141 | 1.650% v/v isopropanol |
| 142 | 1.650% v/v PEG-400 |
| 143 | 1.650% v/v isopropanol |
|  | 660.000 mM Li2 sulfate |
| 144 | 660.000 mM Li2 sulfate |
|  | 1.650% v/v PEG-400 |
| 145 | 660.000 mM Li2 sulfate |
|  | 2.640% v/v MPD |
| 146 | 660.000 mM Li2 sulfate |
|  | .660% v/v PEG-400 |
| 147 | 4.950% v/v MPD |
|  | 330.000 mM Li2 sulfate |
| 148 | 8.250% v/v MPD |
| 149 | 495.000 mM (NH4)2 sulfate |
|  | 3.960% v/v isopropanol |
| 150 | 9.900% v/v isopropanol |
|  | 429.000 mM NaCl |
| 151 | 1320.000 mM NaCl |
|  | 3.300% v/v PEG-400 |
| 152 | 6.600% v/v PEG-400 |
| 153 | 4.950% v/v isopropanol |
| 154 | 4.950% v/v isopropanol |
|  | 0.825% w/v PEG-3350 |
|  | 660.000 mM Sodium formate |
| 155 | 9.900% v/v MPD |
|  | 8.250% w/v PEG 1500 |
| 156 | 9.900% v/v MPD |
|  | 4.950% w/v PEG-8000 |
| 157 | 9.900% v/v MPD |
|  | 3.300% v/v PEG-3350 |
| 158 | 9.900% v/v MPD |
|  | 1.320% w/v PEG 1500 |
| 159 | 9.900% v/v MPD |
|  | 2.640% w/v PEG-8000 |
| 160 | 9.900% v/v isopropanol |
|  | 1.320% w/v PEG-3350 |
| 161 | 3.300% v/v PEG 1500 |
|  | 9.900% v/v isopropanol |
| 162 | 4.950% w/v PEG-8000 |
|  | 13.20% v/v isopropanol |
| 163 | 6.600% v/v isopropanol |
|  | 4.950% w/v PEG-3350 |
| 164 | 9.900% v/v isopropanol |
|  | 9.900% w/v PEG-3350 |
| 165 | 6.600% w/v PEG-8000 |
|  | 13.200% v/v PEG-400 |
| 166 | 13.200% v/v PEG-400 |
|  | 1.650% w/v PEG-3350 |
| 167 | 4.950% w/v PEG 1000 |
|  | 13.20% v/v PEG-400 |
| 168 | 2.640% w/v PEG-8000 |
|  | 13.20% v/v PEG-400 |
| 169 | 8.250% v/v PEG-400 |
|  | 6.600% w/v PEG-3350 |
| 170 | .990% v/v MPD |
|  | 9.900% w/v PEG 1500 |
| 171 | 9.900% w/v PEG 1500 |
|  | 3.300% v/v isopropanol |
| 172 | 9.900% w/v PEG 1500 |
|  | 6.600% v/v PEG-400 |
| 173 | 2.640% v/v MPD |
|  | 9.900% w/v PEG 1500 |
| 174 | 4.950% v/v isopropanol |
|  | 8.250% w/v PEG-3350 |
| 175 | 1.650% v/v PEG-400 |
|  | 8.250% w/v PEG-3350 |
| 176 | 4.950% v/v MPD |
|  | 8.250% w/v PEG-3350 |
| 177 | 8.250% w/v PEG-3350 |
|  | 1.320% v/v isopropanol |
| 178 | 6.600% w/v PEG-8000 |
|  | 3.300% v/v PEG-400 |
| 179 | .990% v/v MPD |
|  | 6.60% w/v PEG-8000 |
| 180 | 6.600% w/v PEG-8000 |
|  | 3.300% v/v isopropanol |
| 181 | 6.600% w/v PEG-8000 |
|  | 6.600% v/v PEG-400 |
| 182 | 8.250% w/v PEG-3350 |
|  | 693.000 mM Sodium formate |

-continued

| Reagent | Precipitating agents |
|---|---|
| 183 | 247.500 mM (NH4)2 sulfate |
|  | 1.650% v/v isopropanol |
|  | 2.475% w/v PEG-3350 |
| 184 | 0.330% w/v PEG-4000 |
| 185 | .495% v/v MPD |
|  | 3.960% w/v PEG 1500 |
|  | 825.000 mM NaCl |
| 186 | 660.000 mM NaCl |
|  | 6.600% w/v PEG-3350 |
| 187 | 1.320% w/v PEG-8000 |
|  | 990.000 mM Sodium formate |
| 188 | 0.165% w/v PEG-4000 |
| 189 | 3.300% w/v PEG-3350 |
| 190 | 0.660% w/v PEG-8000 |
| 191 | 1.650% w/v PEG-4000 |
|  | 2000.000 mM NaCl |
| 192 | 4.950% w/v PEG-8000. |

58. An automated system for identifying a reagent in which a preselected compound crystallizes, comprising:
   (a) a robotic arm and a robotic arm controller which positions said robotic arm;
   (b) a system controller communicating with said robotic arm controller to control movement of said robotic arm, said system controller having a user interface for a user to design, schedule, optimize and/or monitor the operation of said system; and
   (c) an apparatus, under the control of said system controller, for introducing, storing and/or manipulating a plurality of reagents, wherein
   (i) each reagent is in a separate compartment;
   (ii) each reagent comprises a predetermined concentration of each of two types of precipitating agents selected from the group consisting of a first type of precipitating agent which alters the activity coefficient of water, a second type of precipitating agent which increases the molecular crowding of a compound in solution, and a third type of precipitating agent which reduces the dielectric of a solution solvating the compound, wherein for any reagent which contains the same two precipitating agents as one or more other reagents the concentration of at least one of the precipitating agents is different from the concentration of such precipitating agent in any such other reagent.

59. The system of claim 58, further comprising:
   (a) an apparatus, under the control of said system controller, for contacting each of the plurality of reagents with the compound; and/or
   (b) an apparatus, under the control of said system controller, for identifying the presence of a crystal in a reagent with which the compound has been contacted.

* * * * *